(12) United States Patent
Jabbari

(10) Patent No.: US 10,723,774 B2
(45) Date of Patent: *Jul. 28, 2020

(54) KERATIN-BASED HYDROGELS

(71) Applicant: University of South Carolina, Columbia, SC (US)

(72) Inventor: Esmaiel Jabbari, Rockville, MD (US)

(73) Assignee: University of South Carolina, Columbia, SC (US)

(*) Notice: Subject to any disclaimer, the term of this patent is extended or adjusted under 35 U.S.C. 154(b) by 274 days.

This patent is subject to a terminal disclaimer.

(21) Appl. No.: 15/814,617

(22) Filed: Nov. 16, 2017

(65) Prior Publication Data

US 2018/0251505 A1 Sep. 6, 2018

Related U.S. Application Data

(60) Provisional application No. 62/423,454, filed on Nov. 17, 2016.

(51) Int. Cl.
| | | |
|---|---|---|
| *A61L 27/52* | (2006.01) | |
| *C07K 14/47* | (2006.01) | |
| *C08J 3/075* | (2006.01) | |
| *C08J 3/24* | (2006.01) | |
| *C08J 7/18* | (2006.01) | |

(Continued)

(52) U.S. Cl.
CPC ........ *C07K 14/4741* (2013.01); *A61L 27/227* (2013.01); *A61L 27/26* (2013.01); *A61L 27/38* (2013.01); *A61L 27/52* (2013.01); *C08J 3/075* (2013.01); *C08J 3/243* (2013.01); *C08J 7/18* (2013.01); *C08K 5/0025* (2013.01); *A61L 2400/06* (2013.01); *C07K 14/78* (2013.01); *C08J 2389/00* (2013.01)

(58) Field of Classification Search
CPC ........ A61L 27/227; A61L 27/52; A61L 15/32; C07K 14/4741; C08L 89/04; C08L 89/00; A61K 8/042; A61K 38/1748
See application file for complete search history.

(56) References Cited

U.S. PATENT DOCUMENTS 5,932,552 A * 8/1999 Blanchard .............. A61K 8/042
424/443
6,270,793 B1 * 8/2001 Van Dyke .............. A61K 8/042
424/443

(Continued)

OTHER PUBLICATIONS

Anderson, et al. "Post-Traumatic Osteoarthritis: Improved Understanding and Opportunities for Early Intervention." J. Orthop. Res. 29(6): (2011), pp. 802-809.

(Continued)

*Primary Examiner* — Michael A Salvitti
(74) *Attorney, Agent, or Firm* — Dority & Manning, P.A.

(57) ABSTRACT

Keratin-based hydrogels and aqueous compositions and methods for forming the hydrogels and compositions are described. The compositions include solubilized keratin that has been functionalized to include a crosslinking moiety. The crosslinking moiety exhibits controllable crosslinking, e.g., a photopolymerizable crosslinking moiety. The crosslinking functionality is bonded to the keratin via cysteines following reduction of disulfide bonds of the native keratin. The compositions can be injectable and can include living cells and/or other biologically active agents, for instance for use in tissue regeneration.

23 Claims, 7 Drawing Sheets

Specification includes a Sequence Listing.

(51) Int. Cl.
A61L 27/22 (2006.01)
A61L 27/26 (2006.01)
C08K 5/00 (2006.01)
A61L 27/38 (2006.01)
C07K 14/78 (2006.01)

(56) References Cited

U.S. PATENT DOCUMENTS

| | | | | |
|---|---|---|---|---|
| 6,274,155 | B1* | 8/2001 | Van Dyke | A61K 8/042 |
| | | | | 424/402 |
| 6,461,628 | B1* | 10/2002 | Blanchard | A61K 8/042 |
| | | | | 424/402 |
| 6,884,432 | B2 | 4/2005 | Yaszemski et al. | |
| 7,001,987 | B2* | 2/2006 | Van Dyke | A61K 38/015 |
| | | | | 530/350 |
| 7,642,300 | B2 | 1/2010 | Yaszemski et al. | |
| 7,732,574 | B2* | 6/2010 | Kelly | A61K 38/39 |
| | | | | 424/445 |
| 9,101,654 | B2 | 8/2015 | Jabbari | |
| 9,314,549 | B2 | 4/2016 | Jabbari | |
| 9,808,555 | B2 | 11/2017 | Jabbari | |
| 2007/0043202 | A1 | 2/2007 | Yaszemski et al. | |
| 2008/0038327 | A1* | 2/2008 | Kelly | A61K 38/39 |
| | | | | 424/445 |
| 2008/0206308 | A1 | 8/2008 | Jabbari et al. | |
| 2008/0249451 | A1* | 10/2008 | Branham | A61L 15/42 |
| | | | | 602/42 |
| 2009/0324722 | A1* | 12/2009 | Elisseeff | A61K 31/765 |
| | | | | 424/487 |
| 2010/0084784 | A1 | 4/2010 | Jabbari | |
| 2010/0086607 | A1 | 4/2010 | Jabbari | |
| 2010/0137241 | A1* | 6/2010 | Elisseeff | C08F 8/30 |
| | | | | 514/54 |
| 2010/0322979 | A1 | 12/2010 | Jabbari | |
| 2010/0327494 | A1 | 12/2010 | Jabbari | |
| 2012/0226295 | A1 | 9/2012 | Jabbari | |
| 2014/0349367 | A1 | 11/2014 | Jabbari | |
| 2015/0175972 | A1 | 6/2015 | Jabbari | |
| 2018/0251505 | A1* | 9/2018 | Jabbari | C07K 14/4741 |
| 2018/0273899 | A1* | 9/2018 | Jabbari | C12N 5/0068 |

OTHER PUBLICATIONS

Andrades, et al., "Induction of superficial zone protein (SZP)/lubricin/PGR 4 in muscle-derived mesenchymal stem/progenitor cells by transforming growth factor-beta1 and bone morphogenetic protein-7," Arthritis Res. Ther. 14(2): (2012), R72.
Annabi et al., "25th Anniversary Article: Rational Design and Applications of Hydrogels in Regenerative Medicine," Advanced Materials, 26 (2014), pp. 85-124.
Aoyama et al., "Keratin Nanofiber Scaffold for Vascular Graft" (Abstract Only), Tissue Engineering Part A, 21 (2015), p. S244.
Arai et al., "Amino acid sequence of feather keratin from fowl," European Journal of Biochemistry, 132 (1983), pp. 506-507.
Audouin, et al., "Surface-initiated RAFT polymerization of NIPAM from monolithic macroporous polyHIPE," European Polymer Journal 49(5): pp. 1073-1079 (2013).
Balaji et al., "Characterization of keratincollagen 3D scaffold for biomedical applications," Polymers for Advanced Technologies, 23 (2012), pp. 500-507.
Barati et al., "Effect of Organic Acids on Calcium Phosphate Nucleation and Osteogenic Differentiation of Human Mesenchymal Stem Cells on Peptide Functionalized Nanofibers," Langmuir, 31 (2015), pp. 5130-5140.
Barati et al., "Spatiotemporal release of BMP-2 and VEGF enhances osteogenic and vasculogenic differentiation of human mesenchymal stem cells and endothelial colony-forming cells coencapsulated in a patterned hydrogel" Journal of Controlled Release 223 (2016), pp. 126-136.

Barati, et al., "Synthesis and characterization of photocrosslinkable keratin hydrogels for stem cell Encapsulation," Biomacromolecules, 18(2): (2017), pp. 398-412.
Barati et al., "Time dependence of material properties of polyethylene glycol hydrogels chain extended with short hydroxy acid segments," Polymer, 55 (2014), pp. 3894-3904.
Barone et al., "Thermally processed keratin films," Journal of Applied Polymer Science, 97 (2005), pp. 1644-1651.
Bernardes et al., "Facile conversion of cysteine and alkyl cysteines to dehydroalanine on protein surfaces: versatile and switchable access to functionalized proteins," Journal of the American Chemical Society, 130 (2008), pp. 5052-5053.
Bhardwaj et al., "Silk fibroin-keratin based 3D scaffolds as a dermal substitute for skin tissue engineering," Integrative Biology, 7 (2015), pp. 53-63.
Burnett et al., "Hemostatic properties and the role of cell receptor recognition in human hair keratin protein hydrogels," Biomaterials, 34 (2013), pp. 2632-2640.
Chalker et al., "Chemical modification of proteins at cysteine: opportunities in chemistry and biology," Chemistry—An Asian Journal, 4 (2009), pp. 630-640.
Chan et al., "Crosslinking of collagen scaffolds promotes blood and lymphatic vascular stability," Journal of Biomedical Materials Research Part A. 102 (2014), pp. 3186-3195.
Chen et al., "A Universal and Facile Approach for the Formation of a Protein Hydrogel for 3D Cell Encapsulation," Advanced Functional Materials, 25 (2015), pp. 6189-6198.
Chen et al., "Engineering Vascularized Tissue Constructs using an Injectable Cell-laden Collagen Hydrogel" (Abstract Only), Tissue Engineering Part A, 21 (2015), S102.
Dawson et al., "Biomateriais for stem cell differentiation," Advanced Drug Delivery Reviews, 60 (2008), pp. 215-228.
D'Este, et al., "Evaluation of an injectable thermoresponsive hyaluronan hydrogel in a rabbit osteochondral defect model," Journal Biomed. Mater. Res. Part A 104(6) (2010), pp. 1469-1478.
Dong et al., "In Situ "Clickable" Zwitterionic Starch-Based Hydrogel for 3D Cell Encapsulation," ACS Applied Materials & Interfaces, 8 (2016), pp. 4442-4455.
Dong et al., "Injectable Hybrid Hydrogel for Mesenchymal Stem Cell Delivery, from PEG-based Multifunctional Hyperbranched Polymers" (Abstract Only), Tissue Engineering Part A, 21 (2015), S298-S289.
Eastoe, "The amino acid composition of mammalian collagen and gelatin," Biochemical Journal, 61 (1955), p. 589.
Evans, et al., "Use of Genetically Modified Muscle arid Fat Grafts to Repair Defects in Bone and Cartilage," Eur. Cells Mater. 18 (2009), pp. 96-111.
Falah, et al., "Treatment of articular cartilage lesions of the knee." International Orthopaedics, 34(5) (2010), pp. 621-630.
Ferlin et al., "Development of a Dynamic Stem Cell Culture Platform for Mesenchymal Stem Cell Adhesion and Evaluation," Molecular Pharmaceutics, 11 (2014), pp. 2172-2181.
Fraser et al., Keratins: their composition, structure, and biosynthesis: Charles C. Thomas, (1972).
Fuhrmann et al., "Injectable hydrogel promotes early survival of induced pluripotent stem cell-derived oligodendrocytes and attenuates longterm teratoma formation in a spinal cord injury model," Biomaterials, 83 (2016), pp. 23-36.
Fukumoto, et al., "Combined effects of insulin-like growth factor-1 and transforming growth factor-β1 on periosteal mesenchymal cells during chondrogenesis in vitro," Osteoarthritis Cartilage 11(1) (2003), pp. 55-64.
Golub et al., "The Role of Alkaline Phosphatase in Cartilage Mineralization," Bone and Mineral, 17 (1992), pp. 273-278.
Gorman, "Materials Take Wing: What to do with 4 billion pounds of feathers?", Science News, 161 (2002), p. 120.
Grogan, et al., "Zone-Specific Gene Expression Patterns in Articular Cartilage," Arthritis Rheum. 65(2) (2013), pp. 418-428.
Guo et al., "In vitro generation of an osteochondral construct using injectable hydrogel composites encapsulating rabbit marrow mesenchymal stem cells," Biomaterials, 30 (2009), pp. 2741-2752.

(56) References Cited

OTHER PUBLICATIONS

Han et al., "Alkylation of human hair keratin for tunable hydrogel erosion and drug delivery in tissue engineering applications," Acta Biomaterialia, 23 (2015), pp. 201-213.
Han, et al., "Bioerodable PLGA-Based Microparticles for Producing Sustained-Release Drug Formulations and Strategies for Improving Drug Loading," Frontiers Pharmacol. 7 (2016).
Haralson et al., "Extracellular matrix: A practical approach," Annales de Biologie Clinique, (1996), pp. 383-384.
He et al., "Effect of grafting RGD and BMP-2 protein-derived peptides to a hydrogel substrate on osteogenic differentiation of marrow stromal cells," Langmuir, 24 (2008), pp. 12508-12516.
Hoffman, "Hydrogels for biomedical applications," Advanced Drug Delivery Reviews, 64 (2012), pp. 18-23.
Jayathilakan et al., "Utilization of byproducts and waste materials from meat, poultry and fish processing industries: a review." Journal of Food Science and Technology, 49 (2012), pp, 278-293.
Kakkar et al., "Extraction and characterization of keratin from bovine hoof: A potential material for biomedical applications," Springerplus, 3 (2014), p. 596.
Karaman et al., "Effect of surface modification nanofibres with glutamic acid peptide on calcium phosphate nucleation and osteogenic differentiation of marrow stromal cells," Journal of Tissue Engineering and Regenerative Medicine, 10 (2016), pp. E132-E146.
Karimi et al., "A developmentally inspired combined mechanical and biochemical signaling approach on zonal lineage commitment of mesenchymal stem cells in articular cartilage regeneration," Integrative Biology, 7 (2015) pp. 112-127.
Kelly et al., "How to study proteins by circular dichroism," Biochimica et Biophysica Acta (BBA)—Proteins and Proteomics, 1751 (2005), pp. 119-139.
Klein, et al., "Depth-dependent biomechanical and biochemical properties of fetal, newborn, and tissue-engineered, articular cartilage," Journal Biomech. 40(1) (2007), pp. 182-190.
Kwon et al., "In vivo osteogenic differentiation of human turbinate mesenchymal stem cells in an injectable in situ-forming hydrogel," Biomaterials, 35 (2014), pp. 5337-5346.
Lam, et al., "Osteochondral defect repair using bilayered hydrogels encapsulating both chondrogenically and osteogenically pre-differentiated mesenchymal stem cells in a rabbit model," Osteoarthritis Cartilage 22(9) (2014), pp. 1291-1300.
Lee, et al., "Regeneration of the articular surface of the rabbit synovial joint by cell homing: a proof of concept study" Lancet 376 (9739), (2010), pp. 440-448.
Li, et al., "The Effect of Oxygen Tension on Human Articular Chondrocyte Matrix Synthesis: Integration of Experimental and Computational Approaches," Biotechnol. Bioeng. 111(9), (2014), pp. 1876-1885.
Lin et al., "Allyl sulfides are privileged substrates in aqueous cross-metathesis: application to site-selective protein modification," Journal of the American Chemical Society, 130 (2008), pp. 9642-9643.
Long et al., "Improving the mechanical properties of collagen-based membranes using silk fibroin for corneal tissue engineering," Journal of Biomedical Materials Research Part A, 103 (2015), pp. 1159-1168.
Lotz, M.K., "Posttraumatic osteoarthritis: pathogenesis and pharmcological treatment options," Arthritis Res. Ther. 12(3) (2010).
Lv et al., "Structural and functional evaluation of oxygenating keratin/silk fibroin scaffold and initial assessment of their potential for urethral tissue engineering," Biomaterials, 84 (2016), pp. 99-110.
Ma et al., "Enhanced biological stability of collagen porous scaffolds by using amino acids as novel cross-linking bridges," Biomaterials, 25 (2004), pp. 2997-3004.
Mabry et al., "Microarray analyses to quantify advantages of 2D and 3D hydrogel culture systems in maintaining the native valvular interstitial cell phenotype," Biomaterials, 74 (2016), pp. 31-41.
Mak, et al., "Indian hedgehog signals independently of PTHrP to promote chondrocyte hypertrophy," Development 135(11) (2008), pp. 1947-1956.

Mariani, et al., "Signaling Pathways in Cartilage Repair," International Journal of Molecular Science 15(5): (2014), pp. 8667-8698.
Melrose, et al., "Chondroitin sulphate and heparan sulphate sulphation motifs and their proteoglycans are involved in articular cartilage formation during human foetal knee joint development," Histochem. Cell Biol. 138(3): (20112), pp. 461-475.
Mercado, et al., "Effect of grafting BMP2-derived peptide to nanoparticles on osteogenic and vasculogenic expression of stromal cells," Journal of Tissue Eng. Regen. Med. 8(1): (2014), pp. 15-28.
Mi, et al., "Adverse effects of adenovirus-mediated gene transfer of human transforming growth factor beta 1 into rabbit knees," Arthritis Res. Ther. 5(3): (2003), pp. R132-R139.
Moeinzadeh et al., "B13Nanostructure Formation and Transition from Surface to Bulk Degradation in Polyethylene Glycol Gels Chain-Extended with Short Hydroxy Acid Segments," Biomacromolecules, 14 (2013), pp. 2917-2928.
Moeinzadeh, et al. "Comparative effect of physicomechanical and biomolecular cues on zone-specific chondrogenic differentiation of mesenchymal stem cells," Biomaterials 92, (2016), pp. 57-70.
Moeinzadeh et al., "Gelation Characteristics and Osteogenic Differentiation of Stromal Cells in Inert Hydrolytically Degradable Micellar Polyethylene Glycol Hydrogels," Biomacromolecules, 13 (2012), pp. 2073-2086.
Munoz-Pinto et al., "Collagen-mimetic hydrogels promote human endothelial cell adhesion, migration and phenotypic maturation," Journal of Materials Chemistry B. 3 (2015), pp. 7912-7919.
Namba, et al., "Spontaneous repair of superficial defects in articular cartilage in a fetal lamb model." J. Bone Joint Surg. Am. vol. 80A(1): (1998), pp. 4-10.
Nichol et al., "Cell-laden microengineered gelatin methacrylate hydrogels," Biomaterials, 31 (2010), pp. 5536-5544.
Oliver-Welsh, et al, "Deciding how best to treat cartilage defects," Orthopedics 39: (2016), pp. 343-350.
Orth, et al., "Reliability, Reproducibility, and Validation of Five Major Histological Scoring Systems for Experimental Articular Cartilage Repair in the Rabbit Model," Tissue Eng. Part C Methods 18(5): (2012), pp. 329-339.
Pace et al., "A Human Hair Keratin Hydrogel Scaffold Enhances Median Nerve Regeneration in Nonhuman Primates: An Electrophysiological and Histological Study," Tissue Engineering Part A, 20 (2014), pp. 507-517.
Pascher, et al., "Gene delivery to cartilage defects using coagulated bone marrow aspirate," Gene Ther. 11(2): (2004), pp. 133-141.
Patel et al., "Biodegradable polymer scaffold for tissue engineering," Trends in Biomaterials and Artificial Organs, 25 (2011), pp. 20-29.
Pfaff, K. "A third of soldiers disabled after AC1 for lesions in the knee," Orthopedics Today (2014).
Punzi, et al., "Post-traumatic arthritis: overview on pathogenic mechanisms and role of inflammation," Rheumatic Musculoskeletal Dis. 2(2): (2016), p. 279.
Rehmann et al., "Tuning microenvironment modulus and biochemical composition promotes human mesenchymal stem cell tenogenic differentiation," Journal of Biomedical Materials Research Part A, 104 (2016), pp. 1162-1174.
Rivera, et al, "Posttraumatic osteoarthritis caused by battlefield injuries: the primary source of disability in warriors" Journal Am. Acad. Orthp. Surg. 20(1): (2012), pp. S64-S69.
Rivera, et al, "The burden of posttraumatic arthritis," AAOS/OTA/SOMOS/ORS Extremity War Injuries VIII: Sequelae of Combat (2013).
Rouse et al., "A Review of Keratin-Based Biomaterials for Biomedical Applications," Materials, 3 (2010), pp. 999-1014.
Saravanan et al., "Exploration on the Amino Acid Content and Morphological Structure in Chicken Feather Fiber," Journal of Textile and Apparel, Technology and Management, 7-3, (2012).
Sawada et al., "Scaffold for Cell Culture Made by Electrospun Keratin Nanofibers" (Abstract Only), Tissue Engineering Part A, 20 (2014), p. S65.
Simank, et al., "Effects of local application of growth and differentiation factor-5 (GDF-5) in a full-thickness cartilage defect model" Growth Factors 22(1): (2004), pp. 35-43.

(56) References Cited

OTHER PUBLICATIONS

Stenman et al., "Trypsin-2 degrades human type II collagen and is expressed and activated in mesenchymally transformed rheumatoid arthritis synovitis tissue," American Journal of Pathology, 167 (2005), pp. 1119-1124.
Stockwell, R.A. "Interrelationship of Cell Density and Cartilage Thickness in Mammalian Articular Cartilage," Journal of Anatomy 109: (1971), pp. 411-421.
Studer, et al., "Molecular and Biophysical Mechanisms Regulating Hypertrophic Differentiation in Chondrocytes and Mesenchymal Stem Cells," Eur. Cells Mater. 24: (2012), pp. 118-135.
Tan et al., "Fabrication and Evaluation of Porous Keratin/chitosan (KCS) Scaffolds for Effectively Accelerating Wound Healing," Biomedical and Environmental Sciences, 28 (2015), pp. 178-189.
Tanabe et al., "Fabrication and characterization of chemically crosslinked keratin films," Materials Science and Engineering: C, 24 (2004), pp. 441-446.
Tropel et al., "Isolation and characterization of mesenchymal stem cells from adult mouse bone marrow," Experimental Cell Research, 295 (2004), pp. 395-406.
Verma et al., "Preparation of scaffolds from human hair proteins for tissue-engineering applications," Biomedical materials, 3-2 (2008), 025007.
Verschure, et al., "Localization of insulin-like growth factor-1 receptor in human normal and osteoarthritic cartilage in relation to proteoglycan synthesis and content," Br. J. Rheumatol. 35(11): (1996), pp. 1044-1055.
Visser, et al., "Crosslinkable Hydrogels Derived from Cartilage, Meniscus, and Tendon Tissue" Tissue Eng. Part A 21(7-8): (2015), pp. 1195-1206.
Wagegg, et al., "Hypoxia Promotes Osteogenesis but Suppresses Adipogenesis of Human Mesenchymal Stromal Cells in a Hypoxia-Inducible Factor-1 Dependent Manner," PloS One 7(9): (2012), e46483 10.
Wang et al., "Human keratin hydrogels support fibroblast attachment and proliferation in vitro," Cell and Tissue Research, 347 (2012), pp. 795-802.
Wang, et al., "TGF $\beta$ signaling in cartilage development and maintenance," Birth Defects Res. Part C Embryo Today Rev. 102(1): (2014), pp. 37-51.
Watson, et al., "Gene delivery of TGF-$\beta$ 1 induces arthrofibrosis and chondrometaplasia of synovium in vivo," Laboratory Investigation, 90(11):(2010), pp. 1615-1627.
Wehling, et al., "Interleukin-1 $\beta$ and Tumor Necrosis Factor c$\alpha$ Inhibit Chondrogenesis by 16 Human Mesenchymal Stem Cells Through NF-$\kappa$ B-Dependent Pathways," Arthritis Rheum. 60(3): (2009), pp. 801-812.
Williamson, et al., "Growth of immature articular cartilage in vitro: Correlated variation in tensile biomechanical and collagen network properties," Tissue Eng. 9(4): (2003), pp. 625-634.
Wong, et al., "Chondrocyte biosynthesis correlates with local tissue strain in statically compressed adult articular cartilage," Journal of Orthop. Res. 15(2): (1997), pp. 189-196.
Wu, et al. "Human developmental chondrogenesis as a basis for engineering chondrocytes from pluripotent stem cells," Stem Cell Reports 1(6): (2013), pp. 575-589.
Xu et al., "Water-Stable Three-Dimensional Ultrafine Fibrous Scaffolds from Keratin for Cartilage Tissue Engineering," Langmuir, 30 (2014), pp. 8461-8470.
Yamauchi et al., "Preparation of stable aqueous solution of keratins, and physiochemical and biodegradational properties of films," Journal of Biomedical Materials Research, 31 (1996), pp. 439-444.
Yang, et al., "Engineering Orthopedic Tissue Interfaces," Tissue Engineering Part B Rev. 15(2): (2009), pp. 127-141.
Yin et al., "Study on effective extraction of chicken feather keratins and their films for controlling drug release," Biomaterials Science, 1 (2013), pp. 528-536.
Yue et al., "Synthesis, properties, and biomedical applications of gelatin methacryloyl (GelMA) hydrogels," Biomaterials, 73 (2015), pp. 254-271.
Zhang, et al., "The role of tissue engineering in articular cartilage repair and regeneration," Crit. Rev. Biomed. Eng. 37(1-2): (2009), pp. 1-57.

\* cited by examiner

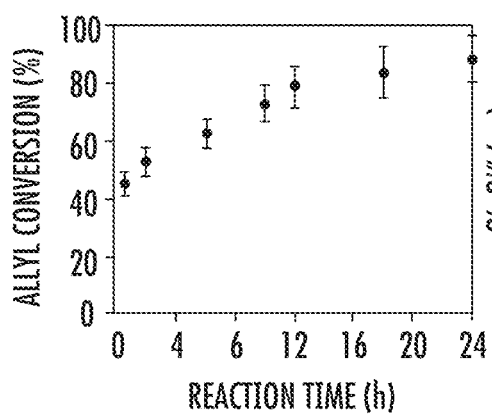
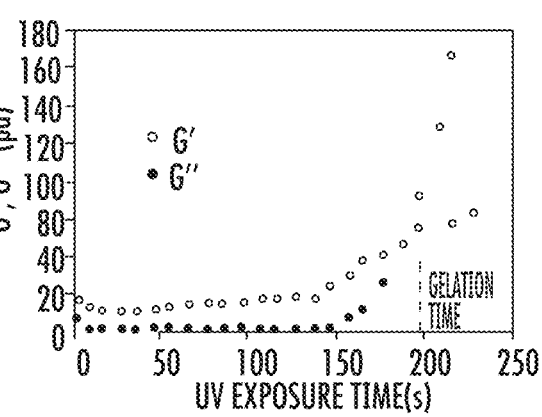
FIG. 3A
FIG. 3B
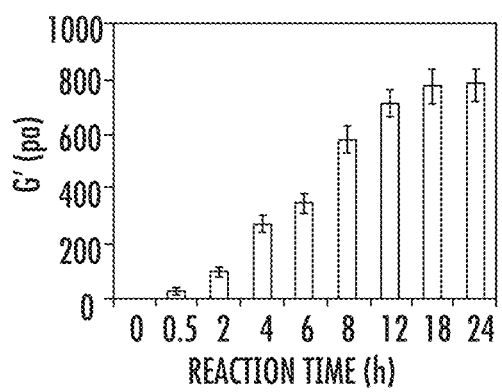
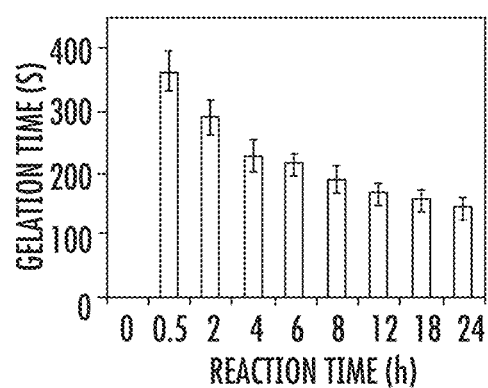
FIG. 3C
FIG. 3D

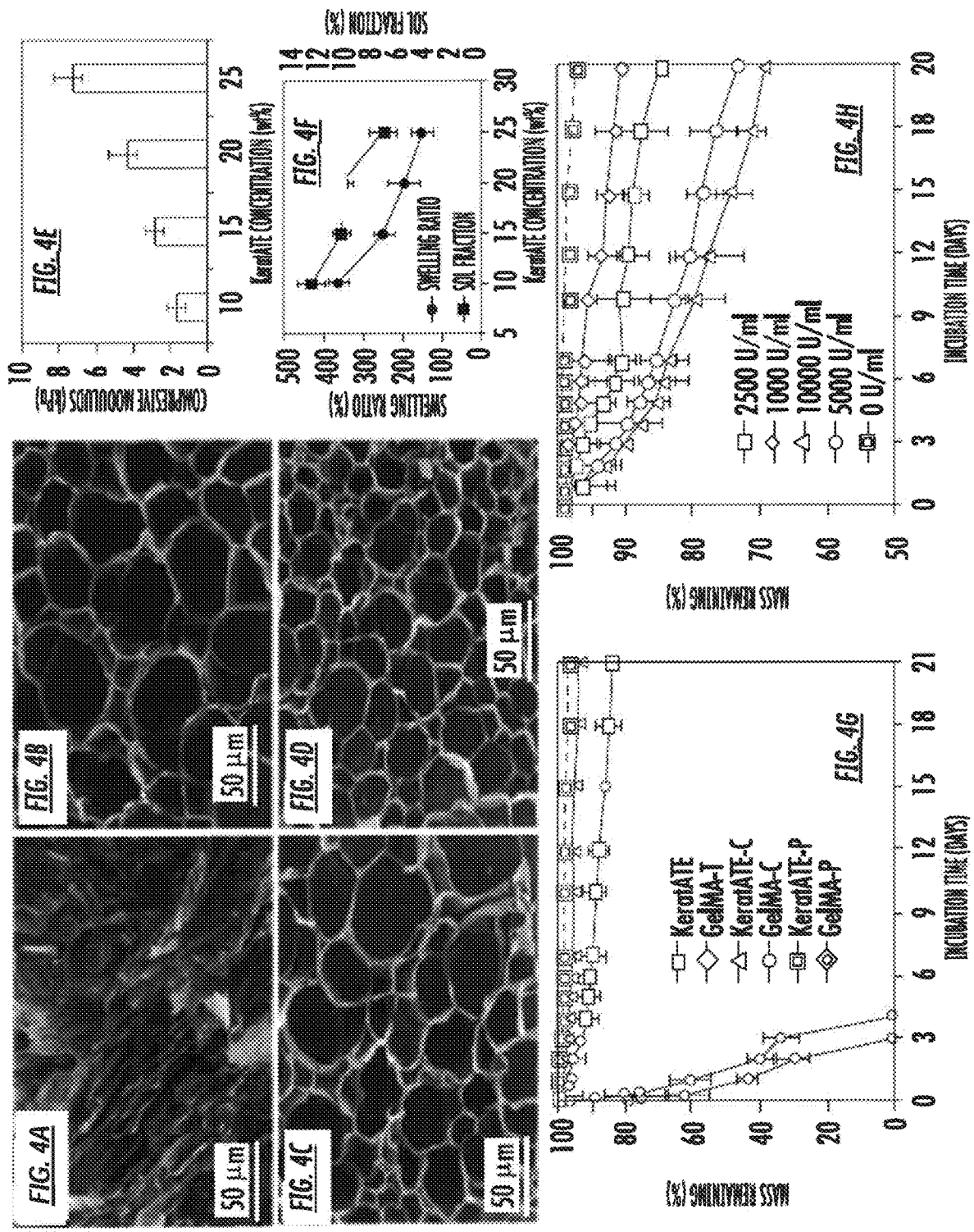

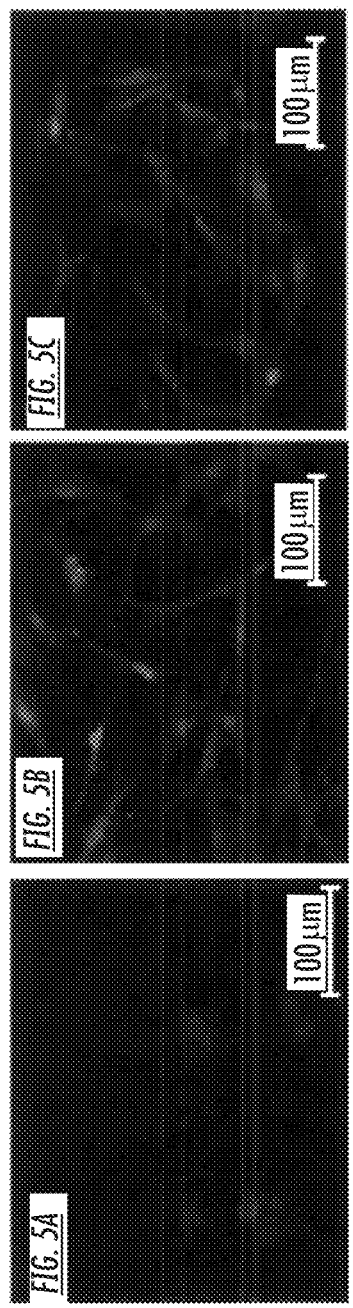
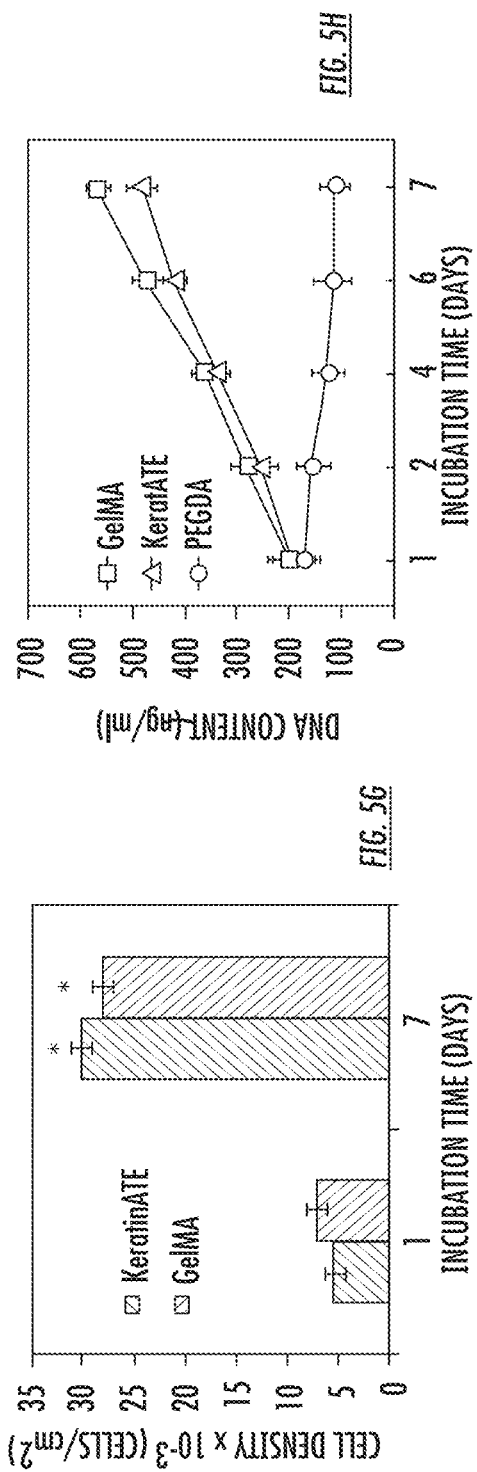

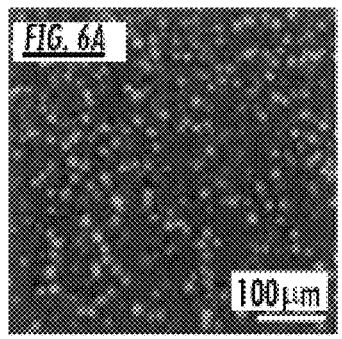
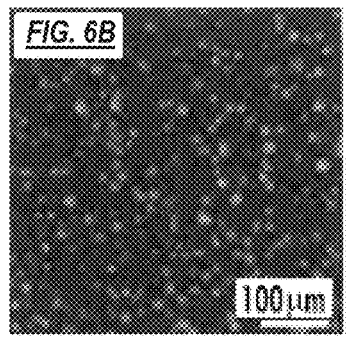
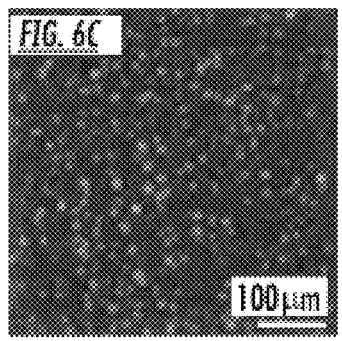
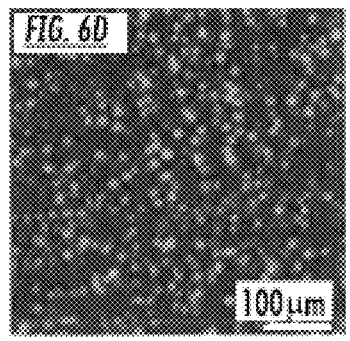
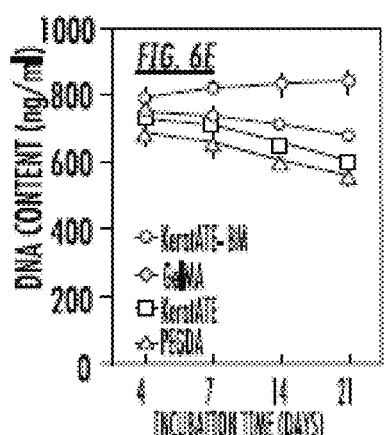
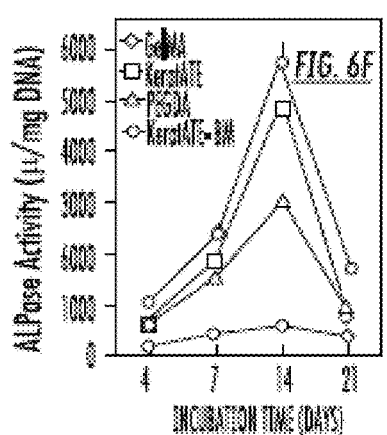
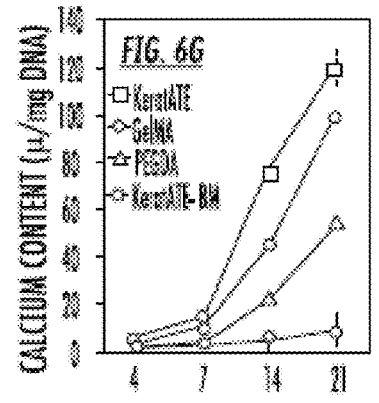
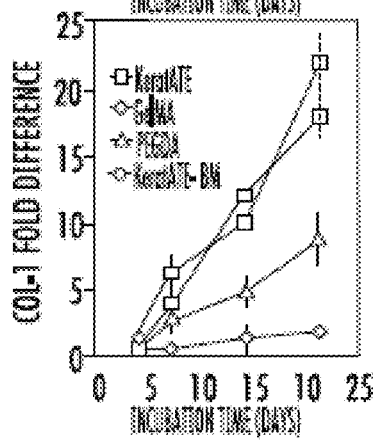
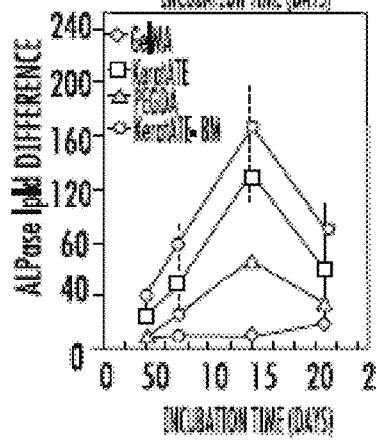
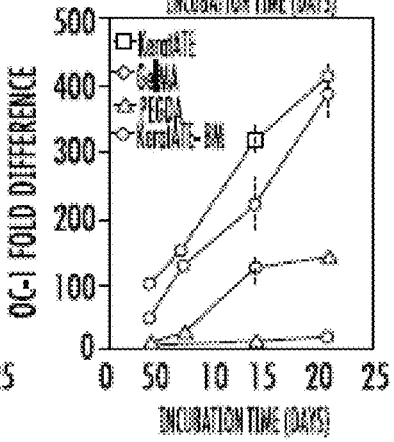

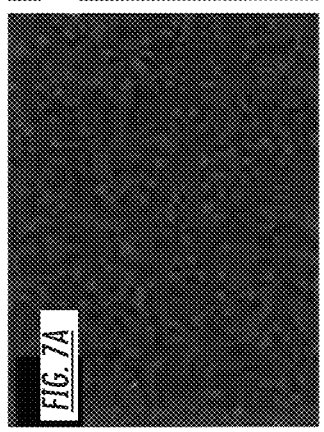
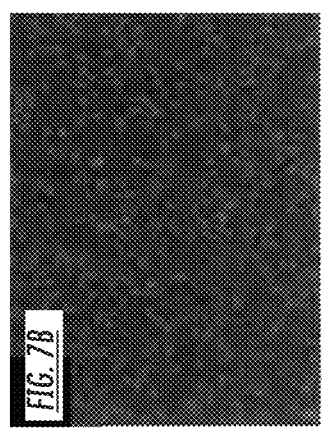
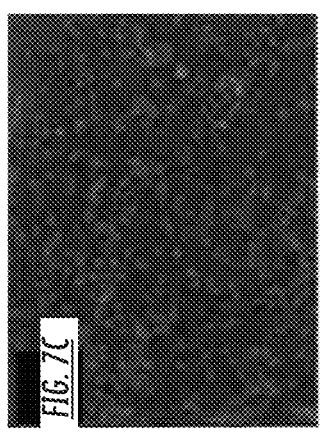
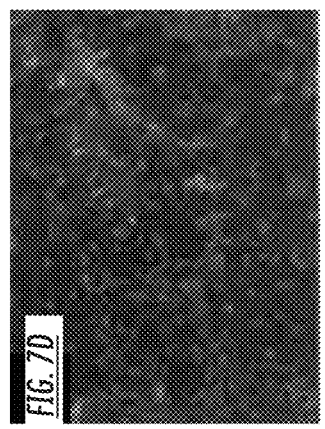
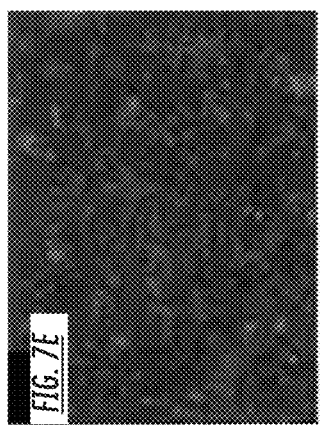
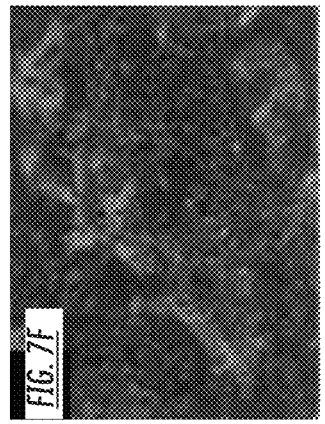
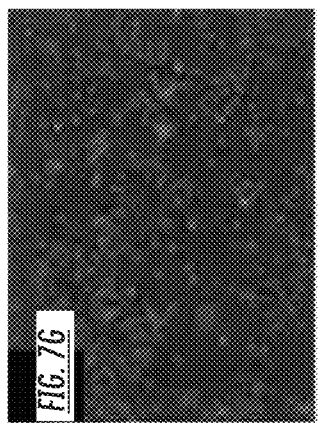
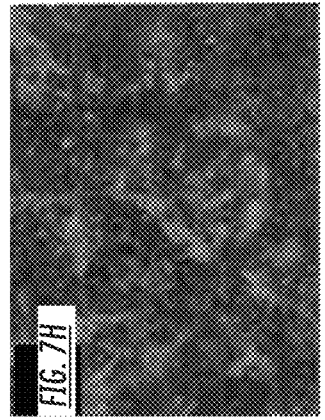

KERATIN-BASED HYDROGELS

CROSS REFERENCE TO RELATED APPLICATION

This application claims filing benefit of U.S. Provisional Patent Application Ser. No. 62/423,454 having a filing date of Nov. 17, 2016, which is incorporated herein by reference for all purposes.

SEQUENCE LISTING

The instant application contains a Sequence Listing which has been submitted electronically in ASCII format and is hereby incorporated by reference in its entirety. Said ASCII copy, created on Feb. 15, 2018, is named USC-527_SL.txt and is 2,238 bytes in size.

BACKGROUND

Hydrogels are three-dimensional networks that include a polymeric continuous phase that can retain a significant volume of water as the dispersed phase and as such resemble the extracellular matrix (ECM) of soft tissues. Hydrogels have been found useful as matrix materials in tissue engineering due to their high diffusivity of, e.g., nutrients and biomolecules. As successful tissue generation will include the formation of new tissue, useful tissue engineering hydrogels must be capable of degradation in order to provide necessary free volume for the newly generated tissue. Synthetic hydrogels that allow for a high water content such as those based on polyvinyl alcohol (PVA), polyhydroxyethyl methacrylate (PHEMA), polyethylene glycol (PEG) and polyvinylpyrrolidone (PVP) have been examined for use in tissue engineering applications. Although synthetic hydrogels can provide matrices with tunable properties, they have little resemblance either structurally or chemically to the natural ECM. Moreover, viability and fate of encapsulated cells in such hydrogels have been limited by the toxic effect of gelation and degradation reactions of the polymer matrix.

Consequently, natural hydrogels derived from components of the ECM that crosslink and degrade enzymatically with no toxic side effects have been preferred for use in clinical applications such as tissue generation. For instance, injectable hydrogel-forming compositions based on natural polymers that are capable of in-situ gelation are highly attractive for use in minimally-invasive arthroscopic procedures, such as in delivery of regenerative cells to irregularly-shaped reconstruction sites. To date, injectable hydrogel forming compositions based on collagen, gelatin and composites thereof that include other natural biopolymers have been used as injectable gels for cell encapsulation and delivery in tissue regeneration. Gelatin, which is produced by partial hydrolysis of collagen, is a mixture of proteins with a wide range of molecular weights. Beneficially, hydrogels based on natural ECM polymers can include amino acid sequences involved in cell-matrix interaction for adhesion, growth, differentiation, and maturation of the encapsulated cells. Unfortunately however, collagen-based hydrogels suffer from several issues that prevent their wider successful use such as batch-to-batch variability in composition, limited thermal and mechanical stability, and relatively fast and uncontrollable enzymatic degradation in vivo.

Keratin is an abundant natural protein found in poultry feather, animal hair and horn, and human hair. Due to its high strength and biocompatibility, keratin-based membranes, sponges, and fiber meshes have been developed as scaffolds for tissue engineering applications. Keratin has a relatively high fraction of cysteine residues (generally about 7 mol % to about 20 mol % of the total amino acid content) compared to other proteins, and partial alkylation of sulfhydryl groups of the cysteine residues combined with freeze drying and crosslinking have been used to produce porous keratin hydrogel scaffolds with tunable pore sizes and stiffness for e.g., cell seeding. Unfortunately, keratin-based hydrogel formation techniques do not form a material capable of injection and in situ crosslinking and are thus not compatible with many clinical procedures, for instance for injection in a precursor form in conjunction with a cell suspension followed by in situ crosslinking.

There is a need for natural protein-based hydrogels that include features of the natural ECM with predictable amino acid composition that can be formed with predetermined degradation control and porosity characteristics. Moreover, an injectable precursor composition capable of in situ crosslinking following injection to form the hydrogels at a target site would be of great benefit.

SUMMARY

According to one embodiment, disclosed is an aqueous composition that includes a hydrogel precursor. The hydrogel precursor includes a keratin-based polymer that has been modified from natural keratin. The modifications include reduction of the disulfide bridges of the natural polymer to form sulfhydryl groups such that about 10% or less of the cysteine residues of the polymer are bonded via disulfide linkages and the polymer is solubilized in the aqueous composition. The keratin-based polymer has also been modified to include reactive functionality on cysteine residues. The reactive functionality can provide crosslinking sites to the polymer. For example, following injection of the composition to a targeted site, the polymer can be crosslinked in situ to form a keratin-based crosslinked hydrogel at the targeted site. The crosslinking can be carried out according to any desired methodology, for instance through addition of energy, e.g., ultraviolet radiation, infrared radiation, etc., to the site, by spontaneous crosslinking at the temperature of the site (e.g., at the natural body temperature of a subject), and/or through inclusion of a chemical crosslinking agent in the hydrogel precursor that is injected to the site in conjunction with the keratin-based polymer. Beneficially, through control of formation parameters of the keratin-based polymer, the crosslinked hydrogel formed from the polymer can have predetermined characteristics such as porosity, degradation characteristics, mechanical characteristic (e.g., compressive modulus), etc.

Also disclosed is a method for forming the aqueous composition. For instance, a method can include modifying a natural keratin by cleaving disulfide bridges between cysteines of the keratin and functionalizing the resulting sulfhydryl groups with a reactive functionality, e.g., an allyl group or the like.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 3A presents the effect of reaction time on conversion of sulfhydryl group of cysteine residues in keratin to S-allyl cysteine.

FIG. 3B presents the effect of UV exposure time on storage (G') and loss (G") modulus of 15 wt. % KeratATE precursor solution (the time at which G' and G" intersect is the gelation time).

FIG. 3C presents the effect of allylation reaction time on G' of 15 wt. % KeratATE hydrogel UV irradiated for 200 seconds.

FIG. 3D presents the effect of allylation reaction time on gelation time of 15 wt. % KeratATE hydrogel precursor solution. Error bars correspond to means±1 standard deviation (SD) for n=3.

FIG. 4A provides SEM images of freeze-dried 25 wt. % KeratATE solution before UV crosslinking.

FIG. 4B provides SEM images of freeze-dried 25 wt. % KeratATE solution after crosslinking with KeratATE concentration of 15 wt. %.

FIG. 4C provides SEM images of freeze-dried 25 wt. % KeratATE solution after crosslinking with KeratATE concentration of 20 wt. %.

FIG. 4D provides SEM images of freeze-dried 25 wt. % KeratATE solution after crosslinking with KeratATE concentration of 25 wt. %, (scale bar in FIG. 4A-FIG. 4D is 50 µm).

FIG. 4E presents the effect of KeratATE concentration on the compressive modulus of the crosslinked hydrogel.

FIG. 4F presents the effect of KeratATE concentration on swelling ratio and sol fraction of the crosslinked hydrogel.

FIG. 4G presents the effect of incubation time on the mass loss of 15 wt. % KeratATE and 10 wt. % GeIMA hydrogels incubated in PBS (P), PBS supplemented with trypsin (T, 2500 USP U/mL) or collagenase (C, 2.5 U/mL).

FIG. 4H presents the effect of trypsin concentration in PBS on mass loss of KeratATE hydrogel with incubation time. Error bars in e-h correspond to means±1 SD for n=3.

FIG. 5A presents DAPI, phalloidin, and vinculin stained images of human mesenchymal stem cells (hMSCs) seeded on PEGDA hydrogels without RGD in basal medium after 1 day incubation.

FIG. 5B presents DAPI, phalloidin, and vinculin stained images of hMSCs seeded on GeIMA hydrogels in basal medium after 1 day incubation.

FIG. 5C presents DAPI, phalloidin, and vinculin stained images of hMSCs seeded on KeratATE hydrogels in basal medium after 1 day incubation.

FIG. 5D presents DAPI, phalloidin, and vinculin stained images of hMSCs seeded on PEGDA hydrogels without RGD in basal medium after 7 days incubation.

FIG. 5E presents DAPI, phalloidin, and vinculin stained images of hMSCs seeded on GeIMA hydrogels in basal medium after 7 days incubation.

FIG. 5F presents DAPI, phalloidin, and vinculin stained images of hMSCs seeded on KeratATE hydrogels in basal medium after 7 days incubation. (scale bars on FIG. 5A-FIG. 5F are 100 µm). The bright dots in FIG. 5E and FIG. 5F show focal adhesion points.

FIG. 5G presents the density of hMSCs on the surface of PEGDA, GeIMA, and KeratATE hydrogels after 1 and 7 day incubation.

FIG. 5H presents the DNA content of hMSCs seeded on PEGDA, GeIMA, and KeratATE hydrogels as a function of incubation time. * in FIG. 5A-FIG. 5H represents a statistically significant difference in cell density between day 7 and day 1 for the same hydrogel.

FIG. 6A presents live and dead stained images of hMSCs encapsulated in 10 wt. % GeIMA hydrogel at time zero.

FIG. 6B presents live and dead stained images of hMSCs encapsulated in 10 wt. % KeratATE hydrogel at time zero.

FIG. 6C presents live and dead stained images of hMSCs encapsulated in 10 wt. % GeIMA hydrogel after 8 hours.

FIG. 6D presents live and dead stained images of hMSCs encapsulated in 10 wt. % KeratATE hydrogel after 8 hours.

FIG. 6E presents DNA content of the encapsulated hMSCs.

FIG. 6F presents ALPase activity of the encapsulated hMSCs.

FIG. 6G presents calcium content of the encapsulated hMSCs.

FIG. 6H presents mRNA expression levels of Col-I from the encapsulated hMSCs.

FIG. 6I presents mRNA expression levels of ALP from the encapsulated hMSCs.

FIG. 6J presents mRNA expression levels of OC from the encapsulated hMSCs.

FIG. 7A presents immunostained images of osteogenic marker osteocalcin (OC) for hMSCs encapsulated in KeratATE hydrogel and incubated in basal medium for 4 days (control).

FIG. 7B presents immunostained images of OC for hMSCs encapsulated in KeratATE hydrogel and incubated in basal medium for 21 days (control).

FIG. 7C presents immunostained images of OC for hMSCs encapsulated in PEGDA and incubated in osteogenic medium after 4 days incubation.

FIG. 7D presents immunostained images of OC for hMSCs encapsulated in PEGDA and incubated in osteogenic medium after 21 days incubation.

FIG. 7E presents immunostained images of OC for hMSCs encapsulated in GeIMA and incubated in osteogenic medium after 4 days incubation.

FIG. 7F presents immunostained images of OC for hMSCs encapsulated in GeIMA and incubated in osteogenic medium after 21 days incubation.

FIG. 7G presents immunostained images of OC for hMSCs encapsulated in KeratATE and incubated in osteogenic medium after 4 days incubation.

FIG. 7H presents immunostained images of OC for hMSCs encapsulated in KeratATE and incubated in osteogenic medium after 21 days incubation. Error bars in FIG. 7A-FIG. 7H correspond to means±1 SD for n=3.

Figure 1:
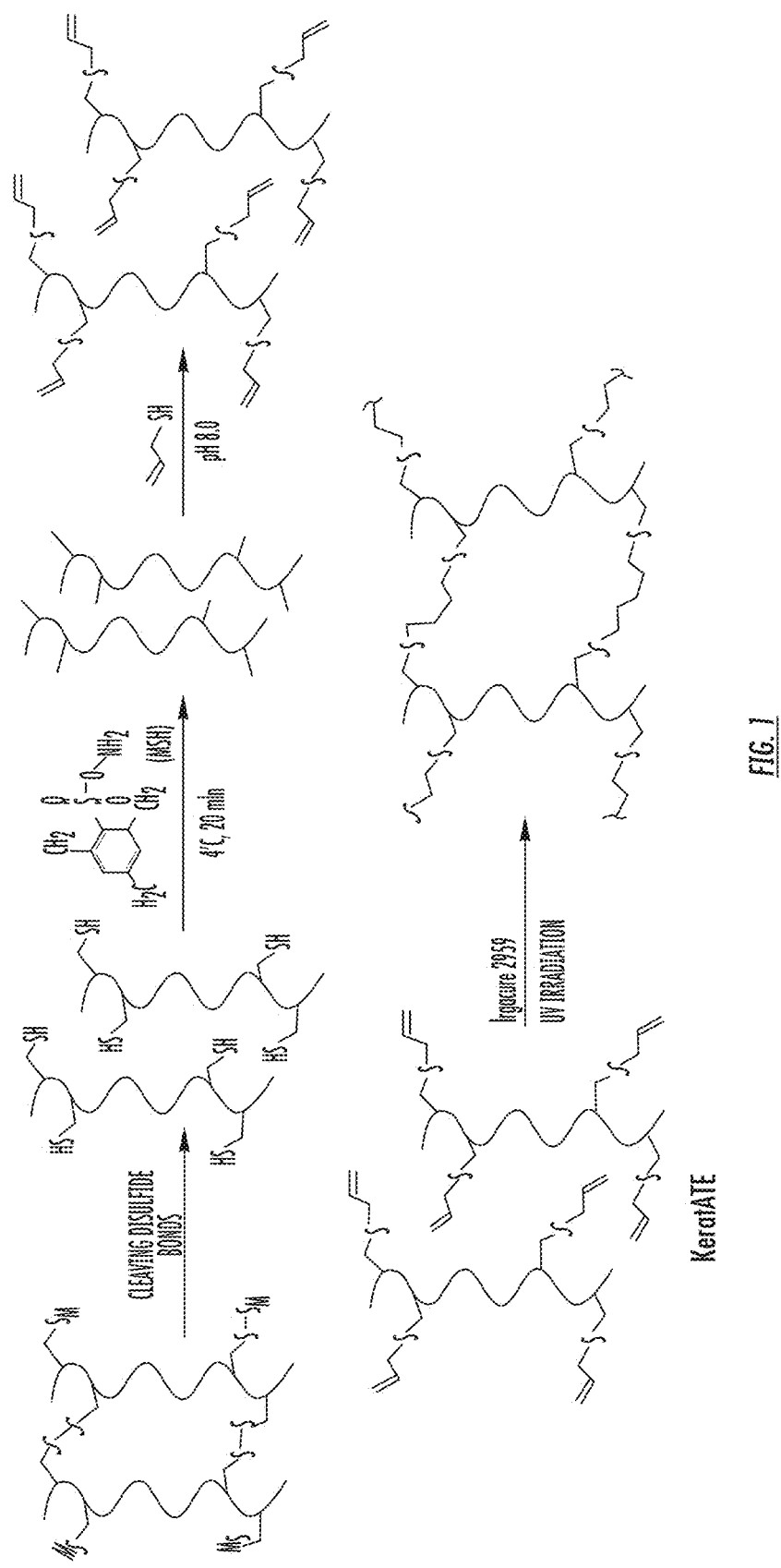
FIG. 1 illustrates a synthesis route for keratin allyl thioether.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is generally directed to the synthesis of injectable aqueous compositions that include a keratin-based hydrogel precursor and the crosslinked hydrogel networks that can be formed with the compositions. Like collagen and gelatin, keratin chains have multiple cell adhesive peptides like Arg-Gly-Asp (RGD), Leu-Asp-Val (LDV) and glutamic acid-aspartic acid-serine (EDS) that can interact with cell surface integrin receptors to promote cell adhesion, differentiation, and maturation. As such, disclosed injectable compositions and hydrogel networks formed by use of the compositions can exhibit excellent biocompatibility, for instance with encapsulated cells and/or with in vivo cells at an injection site.

The compositions can be beneficially utilized in a wide variety of applications such as in situ tissue regeneration. For instance, the keratin-based hydrogels can support adhesion of cells to the same extent or even better than collagen-based hydrogels such as gelatin methacryloyl (GelMA) hydrogels as are known in the art. Moreover, differentiation of cells encapsulated in the keratin-based hydrogels can be similar to that of other biopolymer-based hydrogels and much higher than hydrogels based on synthetic polymers such as RGD-conjugated PEG.

The keratin for use in forming the injectable compositions can be obtained from any natural source. The amount of cysteine residues as compared to the total amino acid content in keratin depends on keratin source and generally varies from about 7% in feather keratin to about 15% in wool keratin, and any keratin source with any cysteine residue content can be utilized. As is known, keratin has a relatively high fraction of cysteine residues as compared to other proteins, and these cysteines are used in the formation of inter- and intra-molecular crosslinks. The disulfide bridges between cysteines in combination with other structural features like crystallinity and hydrogen bonding impart high strength to keratin-based tissues.

To form a keratin-based aqueous composition, keratin can initially be extracted from a natural source. This can be carried out according to known methodology, for instance by breaking disulfide bonds between the individual chains and without hydrolysis of the amide bonds so as to solubilize the keratin. In one embodiment, keratin extraction can be carried out by use of a combination of tris(2-carboxyethyl) phosphine (TCEP), sodium dodecyl sulfate (SDS), and urea. Urea acts as a first solubilizing agent to disrupt intra- and inter-molecular hydrogen bonds in the keratin, TCEP acts as a second solubilizing agent by reducing disulfide bridges to form sulfhydryl groups, and SDS serves a surfactant for stabilization of the solubilized keratin molecules within the aqueous solution.

Of course, the extraction process is not limited to this particular methodology, and any extraction process can be utilized that can reduce disulfide bridges of the natural material without hydrolysis of the protein, so as to produce a relatively monodisperse solubilized protein composition. Following the disulfide bridge reduction, the solubilized keratin polymer can include few or no remaining disulfide bridges. For instance, about 10% or less of the cysteines of the solubilized polymer can be bonded via disulfide bonds.

In general, the solubilized protein chains can include from about 90 to about 100 amino acids and can have a molecular weight of from about 10 kDa to about 12 kDa.

Following extraction, the solubilized keratin polymer can be functionalized to include reactive functionality suitable for crosslinking the polymer and formation of a hydrogel network. More specifically, the reactive functionality can be added to the keratin via reaction of a component carrying the reactive functionality with the sulfhydryl groups of the cysteines and can be such that crosslinking is controllable, i.e., the added reactive functionality will not react at the conditions expected to be encountered during formation, storage, and delivery of the aqueous composition. As such, the composition can be delivered to a site of interest and then caused to crosslink only at the desired time, e.g., following delivery and in situ crosslinking.

The reactive functionality can be configured for crosslinking according to any desirable reaction scheme. In one embodiment, the keratin-based polymer can be modified with a reactive functionality configured for crosslinking via photopolymerization by use of ultraviolet (UV) radiation, infrared (IR) radiation, visible light, or any combination thereof. Examples of photopolymerizable functionality can include, without limitation, allyls, acrylates, diacrylates, oligoacrylates, methacrylates, dimethacrylates, oligomethacrylates, etc., or any combination thereof.

A keratin-based polymer is not limited to photopolymerization, however, and the reactive functionality can be configured for chemical crosslinking, thermal crosslinking, or any other controllable crosslinking reaction scheme or combination thereof in conjunction with or alternative to photopolymerizable functionality. By way of example and without limitation, the polymer can include as reactive functionality carboxylic acids, anhydrides, esters, unsaturated epoxies, etc.

In one embodiment, functionalization of the solubilized keratin can be carried out such that the secondary structure of the keratin is affected to little or no degree. This may be beneficial in providing a crosslinked hydrogel exhibiting a stable, honeycomb-shaped pore structure without the necessity of blending with other polymers such as chitosan, silk fibroin, or collagen (though, as discussed further below, in some embodiments, it may be desirable to form the hydrogel from a combination of natural polymers).

Functionalization of the solubilized keratin polymer can be carried out according to any suitable chemistry. For example, in one embodiment, the sulfhydryl groups of the polymer can be reacted directly with a bi-functional monomer that includes the reactive functionality to form the functionalized polymer in a single-step process. In another embodiment, a multi-step process can be carried out. For instance, in one embodiment described further in the examples section below, a two-step reaction process can be carried out to functionalize sulfhydryl groups of solubilized keratin. In the first step, sulfhydryl groups of cysteines on the keratin can be converted to an intermediate group, for instance by oxidative elimination. In a second step, the intermediate groups can then be converted to include the desired reactive functionality (e.g., an allyl group) and produce the keratin-based polymer as may be crosslinked to form a hydrogel network.

The aqueous composition that includes the functionalized keratin-based polymer can include additional components as desired. For instance, in one embodiment, the polymer can be crosslinked by use of an initiator that is activated by UV radiation (UV initiators), visible light (light initiators), heat (thermal initiators), or chemical initiators. The composition can include the initiator in conjunction with the polymer or an initiator can be combined with the composition at the time of crosslinking. For instance, an initiator can be provided in a separate composition and combined with the aqueous composition that includes the keratin-based polymer at the time of injection of the composition to the site of interest and shortly prior to crosslinking.

Examples of initiators can include, without limitation, acetophenone, 2,2-dimethoxy-2-phenol-acetophenone ("DMPA") (UV initiators), camproquinone, ethyl-4-N,N,-dimethyl aminobenzoate (light initiators), benzoyl peroxide (thermal initiator), or ammonium persulfite (chemical initiator). In one particular embodiment, the photoinitiator can be 4-(2-hydroxyethoxy)phenyl-(2-hydroxy-2-propyl)ketone (Irgacure 2959). Preferred initiators can depend not only upon the particular reactive functionality of the polymer, but also upon the expected application of the hydrogel. For instance, when considered for use for in vivo applications, a suitable initiator for biological use should be utilized.

In some embodiments, the composition can include a crosslinking agent configured for reaction with the reactive functionality of the polymer. A crosslinking agent can be a polyfunctional compound or combination thereof that can react with the reactive functionality of the polymer to form crosslinks within and among the keratin polymers in formation of the hydrogel. In general, a crosslinking agent can be a non-polymeric compound, i.e., a molecular compound that includes two or more reactively functional terminal moieties linked by a bond or a non-polymeric (non-repeating) linking component. By way of example, a crosslinking agent can include but is not limited to di-epoxides, poly-functional epoxides, diisocyanates, polyisocyanates, polyhydric alcohols, water-soluble carbodiimides, diamines, diaminoalkanes, polyfunctional carboxylic acids, diacid halides, and so forth.

A hydrogel formed by crosslinking the reactive functionality of the keratin-based polymer can have a porous, interconnected, honeycomb microstructure. As the natural disulfide bridges of the keratin source are broken and functionalized with a controllable crosslinking moiety in formation of the hydrogel, the product hydrogel can have relatively few disulfide bonds as compared to previously known keratin-based hydrogels. For instance, the keratin-based hydrogels can include about 10% or less of the crosslinks of the hydrogel as disulfide bridges, or even less in some embodiments, for instance about 5% or less, or about 2% or less.

The pore size of the hydrogel can vary, but can generally be about 100 μm or less, for instance from about 10 μm to about 70 μm in some embodiments. Beneficially, the average pore size can be controlled by varying loading level of the keratin-based polymer in the hydrogel precursor solution.

The compressive modulus of the hydrogel can be about 10 kPa or less, for instance from about 1 to about 8 kPa in some embodiments, with modulus being controllable by polymer concentration in the precursor solution.

Degradation rates of the hydrogels can be controlled in one embodiment through inclusion in the hydrogel of other polymers in conjunction with the keratin-based polymer. For instance, trypsin is known to cleave amino acid sequences containing arginine or lysine with long positively-charged side chains. Keratin contains about 4% arginine and no lysine whereas gelatin contains 9% arginine and 4.5% lysine amino acids. Further, gelatin contains -R-Pro-X-Gly-Pro-R-sequence where X is a neutral amino acid that is cleaved by collagenase whereas keratin has no such amino acids and is not targeted by collagenase. As a result, collagenase and trypsin can quickly degrade a hydrogel that includes a collagen-based polymer. Conversely, a keratin-based polymer can degrade relatively slowly in the presence of trypsin and is not susceptible to degradation by collagenase. Accordingly, through blending the disclosed keratin-based polymers with a collagen-based polymer and forming a composite hydrogel network, the degradation rate of the product hydrogel for use in an environment with known trypsin and collagenase concentrations can be controlled based upon the relative amounts of the biopolymers contained in the composite matrix. Thus, hydrogels can be formed having tunable degradation rates for use in particular applications and environments through co-polymerization and/or blends of the functionalized keratin-based polymers with other biopolymers such as collagen based polymers.

In one embodiment, an aqueous composition can be formulated for injection. Typically, the route of injection is subcutaneous or intradermal, although other routes of injection are possible. Formulations suitable for injection are well known in the art, and can, for example, include sterile aqueous solutions and/or dispersions. Formulations can include sesame oil, peanut oil, synthetic fatty acid esters such as ethyl oleate, triglycerides, and/or aqueous propylene glycol and/or sterile powders for the extemporaneous preparation of sterile injectable solutions and/or dispersions. Aqueous injection suspensions may contain substances that increase or decrease the viscosity of the suspension, such as sodium carboxymethyl cellulose, sorbitol, or dextran. Optionally, the suspension may also contain suitable stabilizers or agents that increase the solubility of compounds included in the composition to allow for the preparation of highly concentrated solutions or suspensions where appropriate. In all cases the formulation should be sterile and/or must be fluid to the extent that the composition can pass readily through a syringe and needle of suitable diameter for administration. An injectable composition should generally also be stable under the conditions of manufacture and storage and can include preservatives as known in the art so as to be preserved against the contaminating action of microorganisms, such as bacteria or fungi. Other additives, excipients, and preservatives well known in the art can be used.

The hydrogel networks are well adapted for encapsulating cells. For example, in one embodiment from about $10^6$ to $10^8$ cells/cm$^3$ can be encapsulated within a hydrogel network. Beneficially, as the precursor solution is crosslinkable in situ, in one embodiment, the aqueous composition can be combined with the cells in a suspension. The suspension can then be injected or otherwise located at the site of interest followed by in situ crosslinking so as to form the hydrogel network encapsulating the cells at the site.

In one particular embodiment, the cells can be mammalian cells, for instance human cells. The cell type is not limited. For example, the cells can include, without limitation, connective tissue cells, organ cells, muscle cells, nerve cells, and any combination thereof. In more specific embodiments, the cells can include tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, or bone-forming cells. In some embodiments in which encapsulated cells are non-proliferating cells, the non-proliferating cells can include pancreatic islets, hepatic cells, neural cells, renal cortex cells, vascular endothelial cells, thyroid and parathyroid cells, adrenal cells, thymic cells, ovarian cells, or chondrocytes. In some embodiments, the cells can be stem cells, including but not limited to, bone marrow-derived stem cells, embryonic stem cells, induced pluripotent stem cells, umbilical cord-derived stem cells, placenta-derived stem cells, or amniotic fluid-derived stem cells.

The cells may be engineered to express a target gene product that can be biologically active to provide a chosen biological function, to act as a reporter of a chosen physiological condition, to augment deficient or defective expression of a gene product, or to provide an anti-viral, anti-bacterial, anti-microbial, or anti-cancer activity. The target gene product may be a peptide or protein, such as an enzyme, hormone, cytokine, antigen, or antibody, a regulatory protein, such as a transcription factor, or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may upregulate an endogenous protein, introduce a new protein, or regulate ion concentration by expressing a heterologous ion channel or altering endogenous ion channel function. Examples include, but are not limited to engineered tissues that express gene products which are delivered systemically (e.g., secreted gene products such as proteins including growth factors, hormones, Factor VIII, Factor IX, neurotransmitters, and enkephalins).

In some instances, peptide sequences, growth factors, or hormones may be incorporated within the hydrogel network in order to assist with cell growth and viability. Biodegradable sequences can be incorporated into the networks themselves by functionalizing a degradable sequence with polymerizable groups, most notably acrylate or methacrylate groups, and including this as a co-monomer during network polymerization. A chemically degradable link (e.g., hydrolytically unstable) may cause the network to chemically degrade over time, which can lead to the body's elimination of the hydrogel over time. An enzymatically degradable link may allow degradation to occur when cells reach a certain metabolic state where they secrete such a degradative enzyme. This may allow cells to migrate through the network as they proliferate and possibly replace the gel with native extracellular matrix.

The keratin-based functionalized polymers can provide a viable alternative to collagen based biopolymers as an injectable, polymerizable hydrogel with tunable degradation for encapsulation and delivery of cells, for instance for use in tissue regeneration.

The present disclosure may be better understood with reference to the Examples set forth below.

EXAMPLE

Materials

Chicken feather was obtained from Feathered Egg Company (Portland, Oreg.). Diethyl ether, allyl mercaptan, sodium dodecyl sulfate (SDS) and tris(2-Carboxyethyl) phosphine (TCEP) were purchased from VWR (Bristol, Conn.). 0-(2,4,6-Trimethylbenzenesulfonyl)hydroxylamine (MSH) was purchased from Angene International Limited (London, England). 5,5'-Dithiobis-(2-Nitrobenzoic Acid) (DTNB) reagent was purchased from Sigma-Aldrich (St. Louis, Mo.). All Fmoc-protected amino acids, the Rink Amide NovaGel™ resin and hydroxybenzotriazole (HOBt) were purchased from EMD Biosciences (San Diego, Calif.). 1,1,1,3,3,3-hexafluoro-2-propanol (HFIP), N,N-dimethylformarnide (DMF), dichloromethane (DCM), 4-dimethylaminopyridine (DMAP), diisopropylcarbodiimide (DIC), triisopropylsilane (TIPS), and trifluoroacetic acid (TFA) were received from Acros (Fairfield, Ohio). Phosphate-buffer saline (PBS) and Dulbecco's Modified Eagle's Medium (DMEM) were purchased from GIBCO BRL (Grand Island, N.Y.). Trypsin and fetal bovine serum (FBS) were received from Invitrogen (Carlsbad, Calif.) and Atlas Biologicals (Fort Collins, Colo.), respectively. Collagenase type 3 was purchased from Worthington (Lakewood, N.J.). Vinculin Monoclonal Antibody, Goat Anti-Mouse IgG Antibody-(H+L) FITC Conjugated, Goat Anti-Mouse IgG Antibody-(H+L) Texas-red Conjugated, TRITC-conjugated Phalloidin and 4,6-diarnidino-2-phenylindole (DAPI) were purchased from EMD Millipore (Billerica, Mass.). Mouse anti-human osteocalcin (OC) antibody was purchased from Santa Cruz Biotechnology (Santa Cruz, Calif.). The Live/Dead calcein AM (cAM) and ethidium homodimer-1 (EthD) cell viability/cytotoxicity kit was purchased from Molecular Probes (Life Technologies, Grand Island, N.Y.). The dialysis tubes with molecular weight (MW) cutoff 3.5 kDa, 3-8 kDa and 12-14 kDa were purchased from Spectrum Laboratories (Rancho Dominguez, Calif.). Poly(ethylene glycol) diacrylate (PEGDA, 5 kDa MW) and gelatin methacryloyl (GelMA) were synthesized as described previously. Acrylamide-terminated glycine-arginine-glycine-aspartic acid peptide (Ac-GRGD) (SEQ ID NO: 9) was synthesized on Rink Amide NovaGel™ resin in the solid phase as previously described.

Procedures

Feathers were cleaned by soaking in ether followed by washing with soapy water. The cleaned feathers were dried and cut into small pieces. 1 g of feather was immersed in 100 mL of deionized water (DI) containing 0.5 M SDS, 8 M urea, and 50 mM TCEP. Next, the mixture was heated to 50° C., pH was adjusted to 6.5 and the aqueous solution was continuously stirred for 6 h to cleave disulfide bonds (FIG. 1, first step). Following, the solution was filtered (5 μm pore-size filter paper) and centrifuged at 10,000 rpm to remove undissolved feather. The filtered solution was dialyzed against DI water with a 3.5 kDa molecular weight (MW) cutoff dialysis tube for 3 days at ambient condition with changes in DI water every 6 h. Finally, the keratin solution was frozen and freeze-dried.

A two-step reaction was used to functionalize the treated keratin at cysteine residues. The first reaction was oxidative elimination of sulfhydryl groups of cysteine to dehydroalanine (Dha) using MSH (FIG. 1, second step). Briefly, keratin was dissolved in a 50 mM sodium phosphate buffer supplemented with 1 mM TCEP. Next, the solution was placed in an ice bath and MSH was added to the solution dropwise. The reaction ran for 20 min under stirring. The conversion of cysteine to Dha using MSH is reported to be rapid and reach complete conversion. After heating the mixture to ambient condition, allyl mercaptanol was added to the reaction with the same molar ratio as MSH to convert Dha to S-allyl cysteine (allylation) and form keratin allyl thioether (FIG. 1, third step). The reaction ran for 24 h under stirring. The reaction product was collected in several time intervals between 30 min and 24 h to investigate the effect of reaction time on conversion of Dha. Finally, the product was dialyzed against DI water for 4 days with a change of medium every 6 h and lyophilized. The product Keratin Allyl ThioEther is hereafter denoted herein by KeratATE.

5,5'-dithio-bis-(2-nitrobenzoic acid) (DTNB) test was carried out to quantify the conversion of allyl mercaptanol before and after allylation reaction. Briefly, the DTNB working solution was prepared by mixing DTNB and Tris (0.1 mM) and sodium acetate (2.5 mM) in DI water. Next, 10 μ of the sample solution was mixed with 990 μL DTNB working solution and the optical absorbance was measured at 412 nm. The concentration of free —SH groups was calculated using the calibration curve provided by the manufacturer. Conversion of the allylation reaction was calculated using the following equation:

$$\text{allylation conversion (\%)} = \left[1 - \frac{SHi - SHf}{SHi}\right] \times 100$$

where SHi and SHf are the amount of free —SH before and after the reaction, respectively.

CD spectra were recorded using a model J-720 CD spectrometer Gasco, Tokyo, Japan) with a 1-mm path length at 25° C. The wavelength was 200 nm<λ<240 nm. The sample was prepared by dissolving the freeze-dried keratin in 10 mM phosphate buffer (pH 5) at a concentration of 0.1 mg/mL. The CD spectrum was recorded from 190 to 260 nm at the scan rate of 100 nm/min. The spectrum represents an average of three individual scans. The spectrum obtained from the instrument was converted to specific ellipticity, ([φ]λ/(100 Cl)) where C denotes a concentration of the sample in g/mL and l is the cell length in cm.

SDS-PAGE analysis was used to determine the molecular weight of keratin. Extracted keratin solutions (before and after functionalization) were diluted 1:1 with 2× sample buffer (BioRad, Hercules, Calif.) with 5% 2-mercaptoethanol. The proteins (0.2 mL samples) were separated using a vertical slab gel electrophoretic system with a 4-15% stacking gel. Electrophoresis was performed at 100 V and 15 mA for 90 min. The proteins in the gel were stained with 0.5 g/L Coomassie brilliant blue R-250, 10% acetic acid, and 50% methanol for 1 h and de-stained in 10% acetic acid and 45% ethanol.

TGA analysis of the reduced keratin was performed using a universal V4.4A thermogravimetric analyzer (TA instruments, New Castle, Del.). 3 mg of the sample in $Al_2O_3$ crucibles was heated from 30° C. to 700° C. at the rate of 10° C./min and sample weight was recorded with time.

The molecular weight of keratin was determined qualitatively by dialysis method using dialysis tubes with MW cutoffs of 6-8 kDa and 12-14 kDa. The extracted keratin at a concentration of 10 mg/mL was dissolved in sodium phosphate buffer with 1 mM TCEP. Then, the keratin solution was transferred to the dialysis tube and dialyzed against DI water for 4 days with change of DI water every 6 h. At the end of dialysis, the keratin solution was collected from the tubes, freeze-dried and the protein weight was measured. The percent by weight of protein remaining in the dialysis tube (P) was calculated using the following equation:

$$P = \frac{wi - wf}{wi} \times 100$$

where wi and wf are the initial and final weights of the protein in the dialysis tube.

The functionalized keratin was dissolved in aqueous solution and crosslinked by ultraviolet-initiated polymerization. Briefly, the photo-initiator (Irgacure 2959; CIBA, Tarrytown, N.Y.) was dissolved in PBS at 50° C. by vortexing. The hydrogel precursor solution was prepared by mixing the solution of macromer in PBS (10 mg/mL) with the photo-initiator solution and vortexing. The macromer was KeratATE, GelMA, or PEGDA. The hydrogel precursor solution was degassed and transferred to a polytetrafluoroethylene (PTFE) mold (5 cm×3 cm×750 mm), the mold was covered with a transparent glass plate and fastened with clips. Next, the samples were irradiated with a BLAKRAY 100 W mercury, long wavelength (365 nm) UV lamp (B100-AP, UVP, Upland, Calif.) for 5 min to complete the crosslinking reaction. It should be noted that the UV lamp was used to follow the kinetics of gelation of KeratATE precursor solution whereas the high-intensity Omni Cure UV illumination system was used for cell encapsulation in KeratATE hydrogel (see below). Disk-shaped samples were cut from the gel using an 8-mm cork borer and loaded on the Peltier plate of the TA rheometer and subjected to a uniaxial compressive force at a displacement rate of 7.5 mm/s. The slope of the linear fit to the stress-strain curve for 5%-10% strain was taken as the compressive modulus of the gels.

To measure gelation time, the hydrogel precursor solution was directly loaded on the peltier plate of a TA Instruments AR-2000 rheometer and irradiated at a distance of 10 cm from the sample. A sinusoidal shear strain with frequency of 1 Hz and amplitude of 1% was exerted on the sample and the storage (G') and loss moduli (G") were recorded with time. The time at which G'=G" was recorded as the gelation time.

To measure the swelling ratio and sol fraction of keratin hydrogels, disk shape samples with diameter of 8 mm and thickness of 750 mm were dried at ambient conditions for 12 h followed by drying in vacuum for 1 h at 40° C. After drying, the dry weights (wi) were recorded. Next, the dry samples were swollen in DI water for 24 h at 37° C. with a change of swelling medium every 6 h. After swelling, the surface water was removed and the swollen weights (ws) were measured. Then, the swollen samples were dried as described above and the dry weights (wd) were recorded. The swelling ratio (Q) and sol fraction (S) were calculated from the dry and swollen weights The microstructure of keratin hydrogel was imaged using a VEGA3 SBU variable pressure scanning electron microscope (SEM; Tescan, Kohoutovice, Czech Republic) at 8 KeV accelerating voltage. The lyophilized samples were broken to expose a freshly cut surface for imaging, coated with gold a using a Denton Desk II sputter coater (Moorestown, N.J.) at 20 mA for 75 sec, and imaged with SEM.

Disk shaped samples with diameter of 8 mm and thickness of 750 mm were dried at ambient conditions for 12 h followed by drying in vacuum for 1 h at 40° C. to measure the initial dry weight. Then, the hydrogels were incubated in 5 mL of either PBS, different concentrations of trypsin dissolved in PBS (0, 1000, 2500, 5000, 10000 USP U/mL) or collagenase type 3 dissolved in PBS (2.5 U/ml) at 37° C. under mild agitation. At each time point, samples were washed with DI water to remove excess electrolytes, dried under vacuum, and the dry sample weights were measured and compared with the initial dry weights to determine fractional mass remaining.

hMSCs (Lonza, Allendale, N.J.) were cultivated at 5000 cells/$cm^2$ in a high glucose DMEM medium supplemented with 10% FBS, 100 units/mL penicillin and 100 100 μg/mL streptomycin (basal medium). After reaching 70% confluency, the cells were detached with 0.1% trypsin-0.03% EDTA and sub-cultivated at a ratio of 1:3 for <5 passages, according to supplier's instructions. 24-well tissue culture plates were coated with a thin layer of the hydrogel precursor solution (KeratATE, GelMA, or PEGDA) with a concentration of 15 wt. % in PBS. The precursor solutions in the wells were crosslinked by UV as described above for two minutes. Next, hMSCs were seeded on the surface of the gels at a density of 5×10³ cells/cm² and cultured in basal medium for cell attachment. At each time point (1, 2, 4, 6 and 7 days), cell-seeded hydrogels were washed with serum-free DMEM for 8 h followed by washing with PBS. Next, samples were lysed with 10 mM Tris supplemented with 0.2% triton in PBS and the lysed samples were used for measurement of DNA content using Quant-it PicoGreen. GelMA and PEGDA coated well plates were used as controls.

For cell viability, disks were stained with cAM/EthD live/dead assay (11-IglmL) to image live and dead cells, respectively. Stained samples were imaged with an inverted fluorescent microscope (Nikon Eclipse Ti-E, Nikon, Melville, N.Y.). For immunofluorescent staining, cell seeded hydrogels were washed twice in PBS and fixed with 4% paraformaldehyde (Sigma-Aldrich) at 4° C. for 12 h. Next, samples were permeabilized with 0.1% Triton X-100 and 100 mM glycine in PBS for 1 h and blocked with 1.5% BSA and 0.5 mM glycine in PBS for 2 h. Then, samples were incubated with primary antibody (vinculin monoclonal antibody) in PBS containing 1% BSA for 24 h at 4° C. according to manufacturer's instructions. After washing with PBS, samples were incubated with goat anti-mouse conjugated FITC or goat anti-mouse conjugated Texas-red secondary antibody and TRITC-conjugated phalloidin in blocking buffer for 2 hr at ambient conditions. The cell-seeded hydrogel samples were counter-stained with DAPI to image cell nuclei.

For cell encapsulation, 1×10⁶ hMSCs, suspended in 100 μL of PBS, were added to the KeratATE precursor solution and mixed gently with a pre-sterilized glass rod. The density of MSCs in the gel was 1×10⁶ cells/mL. The mixture was injected between two sterile microscope glass slides and crosslinked by UV irradiation with an OmniCure Series S1500 UV Spot illumination system (200 W lamp) with 8-mm diameter light guide. The high intensity-intensity Omni Cure system was used for cell encapsulation to sharply reduce the crosslinking time and exposure of the encapsulated cells to UV light. The gel precursor solutions were irradiated for 180 s which was the minimum time for the gels to reach their plateau modulus. After crosslinking, the gel samples were cut into disks and the disks were incubated in 2 mL of PBS for 1 h with two medium changes. Next, the medium was replaced with osteogenic medium (basal medium plus 50 μg/mL AA and 10 mM βGP) and hMSCs encapsulated in the gels were incubated for 21 days. Experimental groups included hMSCs encapsulated in KeratATE hydrogel and incubated in basal medium (KeratATE-BM, control group), hMSCs encapsulated in KeratATE hydrogel and incubated in osteogenic medium (KeratATE-OS), hMSCs encapsulated in GelMA hydrogel and incubated in osteogenic medium (GelMA-OS), and hMSCs encapsulated in PEGDA hydrogel and incubated in osteogenic medium (PEGDA-OS). Since PEGDA is non-adhesive, 2 wt. % Ac-GRGD (SEQ ID NO: 9) was added to PEGDA gel precursor solution to impart sites for focal adhesion of encapsulated hMSCs to the matrix. At each time point (4, 7, 14, and 21 days), the samples were evaluated by biochemical, mRNA, and immunohistochemical analysis for the expression of osteogenic markers.

For immunofluorescent staining, the adhered cells on KeratATE disks were washed twice in PBS and fixed with 4% paraformaldehyde (Sigma-Aldrich) at 4° C. for 12 h. Next, samples were permeabilized with 0.1% Triton X-100 and 100 mM glycine in PBS for 1 h and blocked with 1.5% BSA and 0.5 mM glycine in PBS for 2 h. Then, samples were incubated with primary antibody (vinculin monoclonal antibody) in PBS containing 1% BSA for 24 h at 4° C. according to manufacturer's instructions. After washing with PBS, samples were incubated with goat anti-mouse conjugated FITC or goat anti-mouse conjugated Texas-red secondary antibody and TRITC-conjugated phalloidin in blocking buffer for 2 hr at ambient conditions. Each sample was counterstained with DAPI to image the cell nuclei. Stained samples were imaged with an inverted fluorescent microscope (Nikon Eclipse Ti-ε, Nikon, Melville, N.Y.). A similar immunofluorescent staining procedure was used to image the expression of osteocalcin protein (OC) of hMSCs encapsulated in KeratATE hydrogel. For cell viability, the unfixed samples were stained with cAM/EthD live/dead assay (1 μg/mL) and imaged with the inverted fluorescent microscope to image live and dead cells, respectively.

At each time point, part of the MSC-encapsulated KeratATE hydrogel samples were homogenized and sonicated to rupture membranes of the encapsulated cells. Double-stranded DNA (dsDNA) content of the homogenized samples was analyzed using a PicoGreen assay with a plate reader (Synergy HT, Bio-Tek, Winooski, Vt.). Alkaline phosphatase (ALP) activity of the samples was measured with p-nitrophenyl phosphatase (Sigma-Aldrich) with a plate reader at 405 nm. The measured p-nitrophenol concentration was correlated to ALP activity in IU/L and normalized to cell numbers. Calcium content of the samples, as a measure of total mineralized deposit in the sample, was measured using a QuantiChrom Calcium Assay kit with a plate reader at 575 nm.

At each time point, total cellular RNA of encapsulated cells was isolated using TRizol (Invitrogen, Carlsbad, Calif.). 250 ng of the extracted total RNA was subjected to eDNA conversion using the reverse transcription system (Promega, Madison, Wis.). The obtained eDNA was amplified by RT-qPCR with SYBR green RealMasterMix (Eppendorf, Hamburg, Germany) using Bio-Rad CXF96 PCR system (Bio-Rad, Hercules, Calif.) and appropriate gene specific primers. The following forward and reverse primers were designed using Primer3 web-based software and synthesized by Integrated DNA technologies (Coralville, Iowa):

```
Col-I:
Forward:
                                    (SEQ ID NO.: 1)
5'-ATGCCTGGTGAACGTGGT-3'

Reverse:
                                    (SEQ ID NO.: 2)
5'-AGGAGAGCCATCAGCACCT-3'

ALP:
Forward:
                                    (SEQ ID NO.: 3)
5'-ATGGGATGGGTGTCTCCACA-3'

Reverse
                                    (SEQ ID NO.: 4)
5'-CCACGAAGGGGAACTTGTC-3';

OC:
Forward:
                                    (SEQ ID NO.: 5)
5'-ACACTCCTCGCCCTATTG-3'

Reverse:
                                    (SEQ ID NO.: 6)
5'-GATGTGGTCAGCCAACTC-3'

GAPDH:
Forward:
                                    (SEQ ID NO.: 7)
5'-CATGACAACTTTGGTATCGTGG-3'

Reverse:
                                    (SEQ ID NO.: 8)
5'-CCTGCTTCACCACCTTCTTG-3'.
```

The primer sequences were consistent with those previously reported for Col-1, ALP and OC. mRNA expressions were normalized against the reference GAPDH house-keeping gene and fold changes in expression were compared to those for day zero (the day of cell encapsulation).

Data are expressed as means±standard deviation. All experiments were done in triplicate. Significant differences between experimental groups were evaluated using a two-way ANOVA with replication test, followed by a two-tailed Student's t test. A value of $p<0.05$ was considered statistically significant.

Results

Figure 2A:
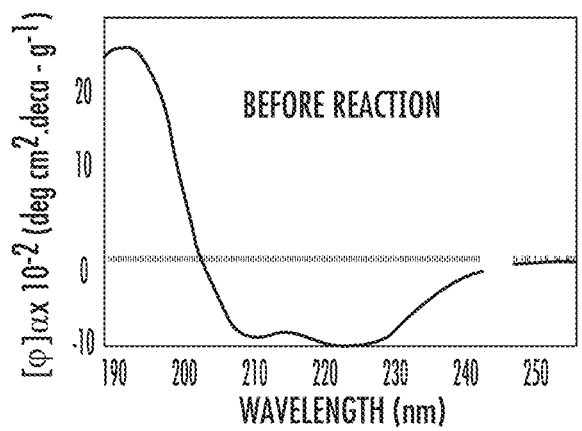
FIG. 2A presents the circular dichroism (CD) spectra of 0.1 mg/mL keratin in phosphate buffer saline before allylation.
Figure 2B:
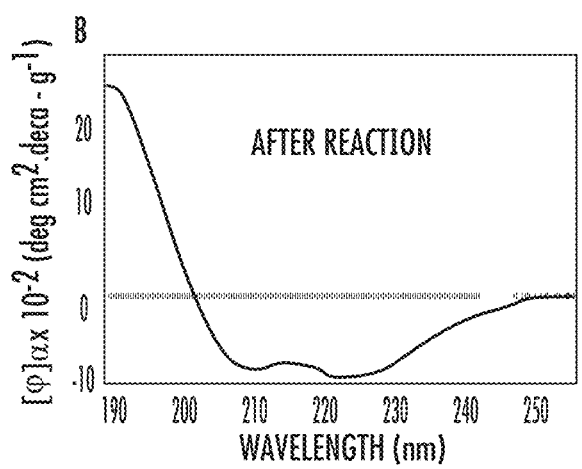
FIG. 2B presents the CD spectra of 0.1 mg/mL keratine in phosphate buffer saline after allylation.

CD spectra of the extracted keratin in aqueous solution before and after allylation reaction are shown in FIG. 2A and FIG. 2B. Negative bands at 208 nm with a shoulder band at 220 nm in both spectra were attributed to α-helical structures in keratin. The broad band in the CD spectra with peak positions at 200 and 235 nm were attributed to β-sheet structures. According to the absorptions in CD spectra, the extracted keratin is composed of α-helical structures with a small fraction of β-sheets in aqueous medium. Further, absence of a significant difference between the spectra of keratin before and after allylation confirmed that functionalization did not affect secondary structure of the keratin.

Figure 2C:
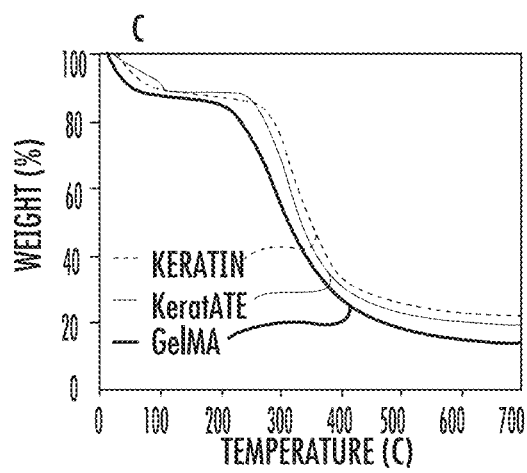
FIG. 2C presents thermal gravimetric analysis (TGA) thermograms of reduced keratin after extraction from chicken feather, modified keratin (KeratATE), and gelatin methacryloyl (GeIMA).

TGA thermographs of extracted keratin after reduction of disulfide bonds, KeratATE after allylation and GelMA are shown in FIG. 2C. The mass loss averaging 8 wt. % and ending at approximately 100° C. was due to loss of moisture from the samples. The moisture content of GelMA was slightly higher than KeratATE. Thermal degradation of GelMA commenced at 180° C. and ended at 400° C. resulting in 68% mass loss. Thermal degradation of reduced keratin and KeratATE commenced at 230° C. and ended at 400° C. resulting in 64% mass loss. There was not a significant difference between the thermographs of reduced keratin and KeratATE. TGA results indicated that KeratATE was thermally more stable than GelMA.

Gel electrophoresis and dialysis were used to estimate molecular weight of extracted keratin before and after functionalization. Electrophoresis patterns of extracted (reduced) keratin before functionalization (K-Oh) and after allylation reaction with different reaction times of 3 h (K-3 h), 12 h (K-12 h), and 24 h (K-24 h) are compared with BSA in FIG. 2D. Based on the pattern for standard molecular weight markers (Ladder, far left column), BSA pattern had a wide range of molecular weights whereas the extracted keratin before functionalization (far right column) showed a narrow band in the 10-15 kDa range. Further, the electrophoretic band for keratin did not change significantly with allylation reaction time (K-3 h, K-12 h, K-24 h).

Figure 2D:
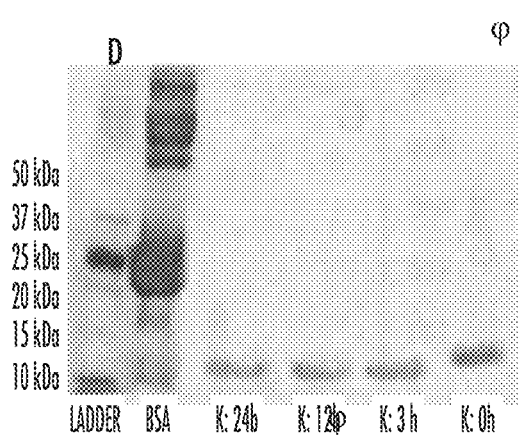
FIG. 2D presents SDS-PAGE from left to right for standard protein MW markers (ladder), bovine serum albumin (BSA), and KeratATE after 24, 12, 3, and zero hours allylation reaction.

Based on the electrophoretic bands, molecular weight of extracted keratin before functionalization was slightly higher than those after allylation which was attributed to residual intermolecular disulfide bridges. The absence of change in the electrophoretic band of keratin with allylation reaction time indicated no degradation or change in molecular structure of extracted keratin with functionalization consistent with CD results. The fraction of extracted keratin dialyzed after 3 days of dialysis is given in Table 1 as a function of MW cutoff of the membrane. As the membrane MW cutoff was increased from 3.5 kDa to 6-8 kDa and 12-14 kDa, the dialyzed fraction increased from zero percent to 6% and 84%, respectively, indicating that the extracted keratin had a narrow MW distribution with 12-14 kDa average MW, consistent with electrophoresis results (FIG. 2D).

TABLE 1

| Molecular weight cutoffs (kDa) | 3.5 | 6-8 | 8-10 |
|---|---|---|---|
| Fraction of keratin inside (wt. %) | 100 | 94 ± 4 | 16 ± 2 |
| Fraction of keratin outside (wt. %) | 0 | 6 ± 1 | 84 ± 5 |

Consistent with previous reports, the oxidative reaction of sulfhydryl groups of keratin with MSH to form Dha was rapid and reached completion in 20 min. The reaction of Dha with allyl mercaptanol was the limiting step in the overall reaction of SH groups to allyl thioether. FIG. 3A shows the effect of reaction time on conversion of Dha to allyl thioether in the extracted keratin. Conversion increased sharply in the first 30 min to 42%, consistent with previous reports, followed by a slower rate of increase in conversion to 78% after 12 h. Conversion increased slightly from 78±3% to 83±4% and 87±3% as reaction time increased to 20 and 24 h.

Effect of UV irradiation time (with low-intensity lamp for rheological experiments) on storage and loss modulus of a 15 wt. % KeratATE precursor solution, as measured by a rheometer, is shown in FIG. 3B. Gelation time of the sample (or the time at which G' reached the same value as G") was 200 s. The effect of allylation reaction time of keratin on the plateau shear modulus of KeratATE precursor solution after UV irradiation (low intensity lamp) is shown in FIG. 3C. G' of the KeratATE gel steadily increased from 40±3 Pa to 780±12 Pa when allylation reaction time increased from 30 min to 12 h. The increase in G' for reaction times >12 h was not significant, consistent with allyl thioether conversion data with reaction time in FIG. 3A. The effect of allylation reaction time on gelation time of 15 wt. % KeratATE precursor solution (low intensity lamp) is shown in FIG. 3D. Gelation time decreased steadily from 360±30 s to 170±15 s as the reaction time increased from 30 min to 12 h while there was insignificant change for reaction times of >12 h. Therefore, based on the results, reaction time of 12 h was selected for allylation of the extracted keratin in subsequent degradation and cell culture experiments.

SEM images for the microstructure of lyophilized hydrogels with 15, 20, and 25 wt. % KeratATE are compared in FIG. 4B, FIG. 4C, and FIG. 4D, respectively. FIG. 4A is an SEM image of lyophilized 25 wt. % KeratATE precursor solution before crosslinking. Due to lack of crosslinking, the microstructure of un-crosslinked KeratATE was mechanically unstable, as can be seen in FIG. 4A. Conversely, the crosslinked KeratATE hydrogels displayed stable, interconnected, honeycomb-like, porous morphology with thin walls (<5 μm thick). Further, the range of hydrogel pore sizes decreased from 35-70 μm to 15-45 μm and 10-35 μm as the concentration of KeratATE in the precursor solution was increased from 15 wt. % to 20 wt. % and 25 wt. %, respectively. The SEM images indicated that microstructure stability and pore size of keratin hydrogels can be controlled by crosslinking.

FIG. 4E and FIG. 4F show the effect of KeratATE concentration in precursor solution on compressive modulus, water swelling ratio, and sol fraction of the hydrogels crosslinked with high-intensity Omni Cure UV system. Compressive modulus of the hydrogels increased from 1.8±0.3 to 7.7±0.4 kPa with increasing KeratATE concentration from 10 to 25 wt. % (FIG. 4E), respectively, whereas swelling ratio in PBS decreased from 390±40% to 150±25% and sol fraction decreased from 12±3% to 7±2%.

FIG. 4G compares mass loss of KeratATE hydrogel (20 wt. %) with GelMA (10 wt. %) in PBS (P), trypsin with 2500

USP U/mL concentration (T), and collagenase with 2.5 U/mL concentration. KeratATE and GeIMA hydrogels showed no mass loss in PBS after 21 days. GeIMA completely degraded in collagenase and trypsin solutions in <5 days. Conversely, KeratATE hydrogel showed <5% mass loss in collagenase solution and 15% mass loss in trypsin after 21 days incubation. FIG. 4H shows that mass loss of KeratATE hydrogel was strongly dependent on trypsin concentration. Mass loss of KeratATE hydrogel increased from 9±3 to 15±4, 26±2 and 30±3 wt. % after 21 days as trypsin concentration in incubation solution was increased from zero to 1000, 2500, 5000 and 10000 U/mL, respectively. The degradation results demonstrate that KeratATE hydrogels possess higher enzymatic stability compared to GeIMA.

Immunostained images in FIG. 5A through FIG. 5F show adhesion of hMSCs to PEGDA (FIG. 5A, FIG. 5D), GeIMA (FIG. 5B, FIG. 5E), and KeratATE (FIG. 5C, FIG. 5F) surfaces after 1 and 7 days. Due to its non-adherent nature, there was little cell adhesion to PEGDA and the attached cells had a round morphology, and there was extensive cell adhesion to GeIMA and the attached cells had elongated spindle-shape morphology. hMSCs seeded on KeratATE had an elongated morphology similar to those seeded on GeIMA after 1 and 7 days. Cell density on KeratATE surface was slightly higher than GeIMA by counting the adherent cells on microscope images (FIG. 5G) but slightly lower than GeIMA by DNA measurement (FIG. 5H). Based on counting the number of stained cells, density of hMSCs on KeratATE surface increased from $5.1\pm0.2\times10^3$ to $29\pm0.5\times10^3$ cells/cm$^2$ with increasing incubation time from 1 to 7 days, respectively, whereas it increased from $7.3\pm0.3\times10^3$ to $27\pm0.6\times10^3$ cells/cm$^2$ for GeIMA. Further, the number of focal cell adhesion points (dots in the images) was significantly higher on KeratATE surface compared to GeIMA (FIG. 5E versus FIG. 5F).

FIG. 6A-FIG. 6D show images of live and dead hMSCs encapsulated in KeratATE and GeIMA hydrogels right after encapsulation (0 h, FIG. 6A and FIG. 6B) and after 8 h (FIG. 6C and FIG. 6D). The fraction of viable hMSCs encapsulated in KeratATE hydrogels, quantified by dividing images into smaller squares and counting the number of live and dead cells, was 99±1% and 92±2% after zero and 8 h, respectively. The fraction of viable hMSCs encapsulated in GeIMA was 99±1% and 94±3% for GeIMA consistent with previously reported >92% viability of fibroblasts in GeIMA.

DNA content, ALPase activity, extent of mineralization (calcium content), mRNA expression levels of Col-I, ALP, and OC for hMSCs encapsulated in KeratATE are compared with GeIMA and PEGDA encapsulated cells in FIG. 6E through FIG. 6J, respectively, with incubation time in osteogenic medium. hMSCs encapsulated in KeratATE and incubated in basal medium without the addition of osteogenic factors (KeratATE-BM) was used as the negative control. For all time points, cell content of KeratATE-BM control group was higher than those groups cultured in osteogenic medium and increased slightly with time. Conversely, cell content of the groups cultured in osteogenic medium (KeratATE, GeIMA, PEGDA) decreased with incubation time consistent with previous reports on reduction in cell content with osteogenic differentiation of hMSCs. KeratATE-BM group in which encapsulated hMSCs were cultured in basal medium had the lowest ALP activity, mineral content (calcium), and lowest mRNA expression of Col-I, ALP, and OC for all time points.

ALP activity of hMSCs in KeratATE, GeIMA, and PEGDA increased from day 4 to 7 and 14 and returned to baseline level after 21 days. Peak ALP activity of hMSCs in KeratATE and GeIMA was significantly higher than PEGDA while ALP activity of hMSCs in KeratATE was slightly lower than GeIMA. Peak ALP activity of hMSCs in KeratATE, GeIMA, and PEGDA after 14 days incubation in osteogenic medium was 4800±90, 5800±150 and 3000±120 IU/mg DNA, respectively (FIG. 6F). Calcium content, as a measure of extent of mineralization of hMSCs in KeratATE was 120±25 mg/mg DNA after 21 days which was higher than hMSCs in GeIMA (100±10 mg/mg DNA) and PEGDA (55±7 mg/mg DNA, FIG. 6G). hMSCs in KeratATE and GeIMA had similar expression of Col-I but their expression was much higher than PEGDA (FIG. 6H). ALP mRNA expression of hMSCs in the hydrogels followed a trend similar to that of ALP activity shown in FIG. 6B. There was not a significant difference between mRNA OC expression of KeratATE (390±30) and GeIMA (410±28) after 21 days but their expression was significantly higher than PEGDA (145±20).

FIG. 7C through FIG. 7H presents immunostained OC images of hMSCs encapsulated in KeratATE (FIG. 7G and FIG. 7H), GeIMA (FIG. 7E and FIG. 7F), and PEGDA hydrogels (FIG. 7C and FIG. 7D) that were incubated in osteogenic medium for either 4 days (top row) or 21 days (bottom row). FIG. 7A and FIG. 7B illustrate hMSCs in KeratATE and incubated in basal medium for 4 days (top) or 21 days, (bottom) as controls. hMSCs in KeratATE and cultured in basal medium showed weak to no OC staining after 21 days whereas hMSCs in PEGDA and cultured in osteogenic medium showed moderate OC staining. Conversely, hMSCs in KeratATE and GeIMA and cultured in osteogenic medium showed strong staining for OC after 21 days, consistent with OC mRNA expressions in FIG. 6J. Taken together, results demonstrated that both KeratATE and GeIMA matrices support osteogenic differentiation of hMSCs.

While certain embodiments of the disclosed subject matter have been described using specific terms, such description is for illustrative purposes only, and it is to be understood that changes and variations may be made without departing from the spirit or scope of the subject matter.

What is claimed is:

1. An aqueous composition comprising a hydrogel precursor, the hydrogel precursor including a solubilized keratin-based polymer comprising reactive functionality bonded to the keratin-based polymer via cysteine residues of the polymer, wherein about 10% or less of the cysteine residues of the solubilized keratin-based polymer are bonded to one another via disulfide bridges.

2. The aqueous composition of claim 1, wherein the reactive functionality comprises allyl functionality, acrylate functionality, diacrylate functionality, oligoacrylate functionality, methacrylate functionality, dimethacrylate functionality, oligomethacrylate functionality, or any combination thereof.

3. The aqueous composition of claim 1, further comprising a crosslink initiator.

4. The aqueous composition of claim 3, wherein the crosslink initiator comprises an ultraviolet initiator, a visible light initiator, a thermal initiator, or a chemical initiator.

5. The aqueous composition of claim 1, further comprising a crosslinking agent.

6. The aqueous composition of claim 1, wherein the composition is sterile.

7. The aqueous composition of claim 1, wherein the composition is injectable.

8. The aqueous composition of claim 1, further comprising living cells.

9. The aqueous composition of claim 1, further comprising a second biologically derived polymer.

10. The aqueous composition of claim 9, wherein the second biologically derived polymer comprises gelatin, chitosan, or alginate.

11. A method for forming the aqueous composition comprising the hydrogel precursor of claim 1, the method comprising:
    combining a keratin polymer with a first solubilizing agent, the first solubilizing agent cleaving disulfide bridges of the keratin polymer and forming sulfhydryl groups on the keratin polymer; and
    functionalizing the keratin polymer via reaction of the sulfhydryl groups, the functionalization including bonding of the reactive functionality at cysteine residues of the keratin polymer to form the keratin-based polymer.

12. The method of claim 11, further comprising combining the keratin-based polymer with a second solubilizing agent, the second solubilizing agent disrupting hydrogen bonds on the keratin-based polymer.

13. The method of claim 11, the reactive functionality comprising allyl functionality, acrylate functionality, diacrylate functionality, oligoacrylate functionality, methacrylate functionality, dimethacrylate functionality, oligomethacrylate functionality, or any combination thereof.

14. The method of claim 11, further comprising combining the functionalized keratin-based polymer with a crosslink initiator.

15. The method of claim 11, further comprising combining the functionalized keratin-based polymer with a crosslinking agent.

16. The method of claim 11, further comprising dispersing living cells into the composition.

17. A method for forming a hydrogel comprising:
    delivering the aqueous composition comprising the hydrogel precursor of claim 1 to a site; and
    following delivery, crosslinking the keratin-based polymer at the site via reaction of the reactive functionality.

18. The method of claim 17, wherein the keratin-based polymer is crosslinked via addition of energy to the site.

19. The method of claim 18, wherein the energy is in the form of ultraviolet radiation, visible light, or infrared radiation.

20. The method of claim 17, wherein the keratin-based polymer is crosslinked via addition of a crosslinking agent to the site.

21. The method of claim 17, wherein the aqueous composition comprising the hydrogel precursor is delivered to the site via injection.

22. The method of claim 17, the aqueous composition further comprising living cells.

23. The method of claim 17, the aqueous composition further comprising a second biopolymer.

\* \* \* \* \*

SEQUENCE LISTING

<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgcctggtg aacgtggt                                                18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aggagagcca tcagcacct                                               19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgggatggg tgtctccaca                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccacgaaggg gaacttgtc                                               19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acactcctcg ccctattg                                                18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatgtggtca gccaactc                                                18

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
catgacaact ttggtatcgt gg                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctgcttcac caccttcttg                                                 20

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Gly Asp
1
```